(12) United States Patent
Kusleika et al.

(10) Patent No.: US 7,384,424 B2
(45) Date of Patent: Jun. 10, 2008

(54) DISTAL PROTECTION DEVICES HAVING CONTROLLABLE WIRE MOTION

(75) Inventors: Richard S. Kusleika, Eden Prairie, MN (US); Daniel Adams, Long Lake, MN (US); Kent D. Anderson, Champlin, MN (US); Dale Nelson, Minneapolis, MN (US); Jeffrey D. Santer, Spring Lake Park, MN (US)

(73) Assignee: ev3 Inc., Plymouth, MN (US)

( * ) Notice: Subject to any disclaimer, the term of this patent is extended or adjusted under 35 U.S.C. 154(b) by 611 days.

(21) Appl. No.: 10/915,171

(22) Filed: Aug. 10, 2004

(65) Prior Publication Data

US 2005/0010247 A1 Jan. 13, 2005

Related U.S. Application Data

(62) Division of application No. 10/093,572, filed on Mar. 8, 2002, now Pat. No. 6,773,448.

(51) Int. Cl.
*A61M 29/00* (2006.01)

(52) U.S. Cl. .................................................. 606/200

(58) Field of Classification Search ................ 606/113, 606/114, 127, 159, 200, 191, 194, 198
See application file for complete search history.

(56) References Cited

U.S. PATENT DOCUMENTS 3,472,320 A * 10/1969 Fogarty ............... 606/127
5,152,777 A   10/1992 Goldberg et al.
5,171,233 A   12/1992 Amplatz et al.
5,484,424 A    1/1996 Cottenceau et al.
5,814,064 A    9/1998 Daniel
5,911,734 A    6/1999 Tsugita et al.
5,980,555 A * 11/1999 Barbut et al. ............... 606/200
6,050,972 A    4/2000 Zadno-Azizi et al.
6,129,739 A   10/2000 Khosravi
6,179,859 B1   1/2001 Bates et al.
6,179,861 B1   1/2001 Khosravi et al.
6,231,588 B1   5/2001 Zadno-Azizi
6,245,012 B1   6/2001 Kleshinski
6,270,477 B1   8/2001 Bagaoisan et al.
6,287,321 B1   9/2001 Jang
6,325,815 B1  12/2001 Kusleika et al.

(Continued)

FOREIGN PATENT DOCUMENTS

EP         0 820 729        1/1998

(Continued)

OTHER PUBLICATIONS

Claims for U.S. Appl. No 08/748,066, filed Nov. 12, 1996.

(Continued)

*Primary Examiner*—Kevin T. Truong
(74) *Attorney, Agent, or Firm*—Popovich, Wiles & O'Connell, P.A.

(57) ABSTRACT

A distal protection device for use in a body lumen. The device includes a functional element which may be a filter or an occlusive element. The device includes means for controlling the movement and placement of the functional element along a guidewire. Motion of the guidewire can be independent of the motion of the functional element.

17 Claims, 21 Drawing Sheets

U.S. PATENT DOCUMENTS

| | | |
|---|---|---|
| 6,336,934 B1 | 1/2002 | Gilson et al. |
| 6,361,546 B1 | 3/2002 | Khosravi |
| 6,371,971 B1 | 4/2002 | Tsugita et al. |
| 6,610,077 B1 | 8/2003 | Hancock et al. |
| 6,616,681 B2 | 9/2003 | Hanson et al. |
| 6,786,888 B1 | 9/2004 | Zadno-Azizi et al. |
| 2001/0012951 A1 | 8/2001 | Bates et al. |
| 2001/0041908 A1 | 11/2001 | Levinson et al. |
| 2002/0022858 A1 | 2/2002 | Demond et al. |
| 2002/0026211 A1 | 2/2002 | Khosravi et al. |
| 2002/0026213 A1 | 2/2002 | Gilson et al. |
| 2002/0072730 A1 | 6/2002 | McGill et al. |
| 2002/0143360 A1 | 10/2002 | Douk et al. |

FOREIGN PATENT DOCUMENTS

| | | |
|---|---|---|
| EP | 1 127 556 A2 | 8/2001 |
| EP | 1 247 500 A2 | 10/2002 |
| WO | WO 96/01591 | 1/1996 |
| WO | WO 98/39053 | 9/1998 |
| WO | WO 99/23976 | 5/1999 |
| WO | WO 00/07657 | 2/2000 |
| WO | WO 00/67669 | 11/2000 |
| WO | WO 00/67671 | 11/2000 |
| WO | WO 01/15629 | 3/2001 |
| WO | WO 01/21100 | 3/2001 |
| WO | WO 01/35857 A1 | 5/2001 |
| WO | WO 01/50982 A1 | 7/2001 |
| WO | WO 01/52768 | 7/2001 |
| WO | WO 01/80777 | 11/2001 |
| WO | 1 181 900 A2 | 2/2002 |
| WO | WO 02/060519 A1 | 8/2002 |

OTHER PUBLICATIONS

Claims for U.S. Appl. No 10/051,565, filed Jan. 18, 2002.
Claims for U.S. Appl. No 10/051,492, filed Jan. 18, 2002.
Claims for U.S. Appl. No 10/051,591, filed Jan. 18, 2002.
Claims for U.S. Appl. No 10/051,537, filed Jan. 18, 2002.
Claims for U.S. Appl. No 10/051,648, filed Jan. 18, 2002.
Claims for U.S. Appl. No 10/060,272, filed Jan. 30, 2002.
Claims for U.S. Appl. No 10/060,271, filed Jan. 30, 2002.
Claims for U.S. Appl. No 09/824,910, filed Apr. 3, 2001.
Claims for U.S. Appl. No 10/060,854, filed Jan. 30, 2002.
International Search Report of PCT/US03/04825 (1 page).
U.S. Appl. No 10/132,562, filed Apr. 25, 2002.
U.S. Appl. No 10/194,355, filed Jul. 12, 2002.
U.S. Appl. No 10/194,734, filed Jul. 12, 2002.
U.S. Appl. No 10/096,624, filed Mar. 12, 2002.

* cited by examiner

DISTAL PROTECTION DEVICES HAVING CONTROLLABLE WIRE MOTION

CROSS-REFERENCE TO RELATED APPLICATION

This Application is a divisional of application Ser. No. 10/093,572, filed Mar. 8, 2002, now U.S. Pat. No. 6,773,448, hereby incorporated herein by reference.

FIELD OF THE INVENTION

This invention relates to devices used in a blood vessel or other lumen in a patient's body. In particular, this invention relates to distal protection devices having a guidewire which can be controlled independently of a functional element such as a filter which is carried by the guidewire.

BACKGROUND OF THE INVENTION

During vascular surgery or endovascular treatment of vessels including atherectomy, balloon angioplasty, and/or stent deployment, debris such as plaque and blood clots can move from the treatment site through a vein or artery, thus compromising the flow of blood at a location distal from the treatment site. Various distal protection systems have been developed to prevent such debris from embolizing in the vessel. Such distal protection devices include filters and occlusive devices, (e.g., balloons) placed distally of the treatment site.

It is desirable to place a distal protection device at a chosen location in order to achieve good sealing between the device and the wall of the vessel. Frequently it is necessary to match the protection device diameter with the vessel diameter, and vessels are known to taper or to have diameters that vary due to disease. It is also desirable to place the protection device in a relatively disease free portion of the vessel so as to minimize liberation of emboli from the wall of the vessel due to interaction with the protection device. Further, it is desirable that the device remains at the desired location during the procedure. Excessive motion of the wire or elongate guide member used to deliver the device can advance a protection device distally, beyond branch vessels, which thereby become unprotected from emboli.

Distal protection devices typically are mounted on a wire or tube that functions as a guidewire. As used herein the term guidewire means either a traditional guidewire or other elongate member or hollow tube that is used in delivering the distal protection device. The protection device can be either a filter or an occlusive device such as a balloon. The distal protection devices are either fixedly attached to the guidewire or attached so as to permit a limited amount of motion between the device and the guidewire. Frequently, the same guidewire used to carry the device is also used to guide various catheters to and from the treatment site. For example, during the procedure, catheters may be exchanged over this guidewire. When catheters are exchanged inadvertent wire movement can cause the protection device to move within the vessel. Excessive wire motion can also retract a protection device proximally, where it can potentially become entangled in a stent or even be inadvertently removed from the vessel being protected. In some vessels, when guide catheters are repositioned, the protection device also tends to move within the vessel. This is undesirable because captured emboli can be released and/or new emboli can be formed distal to the protection device, blood vessels can be damaged, and/or the device can entangle with an implant such as a stent. Therefore, it is clear that too much movement of the device within the vessel could have catastrophic results.

Some work already has been done to provide for limiting the movement of a distal protection device or distal filter with respect to a guidewire. For example, a guidewire having a distal stop is described in WO 01/35857 (Tsugita et al.). The filter slides on the guidewire but cannot slide off the wire due to the distal stop. Another device which includes a slideable vascular filter having both distal and proximal sliding elements that move independently of each other over a mandrel is described in WO 01/21100 (Kusleika et al.) and is illustrated in FIG. 37. The device includes filter F, distal and proximal sliding elements (D and P) at either end of the filter, and stop S, all disposed about mandrel M. Body B of the filter F assumes a generally tubular shape and is made of a resilient material. The proximal length of the filter body has opening O therein. This opening permits body fluid with particulate therein to enter the enclosure formed by body B of the filter. The mandrel is sufficiently flexible so that the device can be deployed in a curving body passageway. The distal-most length of the mandrel is shown having a flexible helically wound coil T thereover. This coil enhances the flexibility of the distal tip. The stop is at a fixed position on the mandrel and thus limits the movement of the sliding elements D and P. The filter is thus allowed to move along the mandrel or guidewire only the distance to the stop. While this system meets many of the needs in the art, it limits the range of motion of the filtration device on the guidewire, and the precision with which it can be placed is limited.

Another known limitation of distal protection devices relates to wire bias. It is well known that a guidewire will conform to the outside of a curved vessel on advancement of the wire in a distal direction and will conform to the interior of a curved vessel during retraction of the wire. Most distal protection devices are attached to wires, and when they are deployed in vessel curvature the wire bias will alternately move the device between the inside and the outside of the vessel curve. For filters this can defeat the protection effect by compressing the filter opening. For occlusion devices the wire bias effect can cause excessive motion of the occlusion device with potential liberation of embolic debris from the vicinity of the occlusive element.

Some work already has been done to provide for limiting the radial movement of a guidewire relative to a distal protection device. For example, a protection device having a proximal loop is described in EP 1, 181,900 A2, (U.S. Ser. No. 09/628,212, Oslund et al.). A loop is provided proximal to the filter to immobilize the wire against the vessel wall regardless of wire bias. While this system meets many of the needs in the art, it adds bulk to the device and thereby limits crossing profile.

It would be desirable to have a distal protection system that can be precisely placed at a location within the vasculature and that can accommodate a wide range of axial and radial wire motion without disturbing the device's position.

SUMMARY OF THE INVENTION

This invention is a distal protection device for use in a body lumen. The device includes a guidewire system which may include separate individual guidewire or elongate members. A functional element, such as a filter or occlusive device including a balloon is mounted on the guidewire system. The device is able to filter or occlude debris and blood clots in a body lumen and/or prevent them from moving distally and causing emboli. The various embodiments of the invention disclosed herein allow the user to accurately place the filter in the vessel and permit substantial guidewire movement during the filter use without dislodging the filter. Motion of the guidewire can be independent of the motion of the distal protection device and the contact force between the guidewire and the protection device can be cushioned in the device of this invention. In addition, in some of the embodiments disclosed herein the user of the device is able to enable or disable the relative motion feature between the guidewire and the protection device and/or to obtain tactile feedback to indicate the limit of the range of guidewire movement when the relative motion feature is enabled.

In a first embodiment, this invention is a distal protection device for use in a body lumen comprising first and second elongate members having distal and proximal ends, a functional element carried by the second elongate member, the functional element being expandable from a delivery configuration to an expanded deployed configuration when the functional element is deployed in the body lumen; and means for moveably connecting the first and second elongate members over a range of motion from a first relative position to a second relative position such that when the functional element is deployed in the lumen the first elongate member may be moved without resulting in corresponding movement of the functional element, the distal end of the second elongate member being distal to the distal end of the first elongate member over the entire range of motion.

The connecting means may comprise a flexible tether. The connecting means may comprise a distal portion of the first elongate member having a lumen which is configured to slideably receive a proximal portion of the second elongate member, the second elongate member having an enlarged proximal end, the lumen of the distal portion having a constricted portion defining an opening which is smaller than the enlarged proximal end of the second elongate member such that the second elongate member is slideably retained in the lumen of the distal portion. The connection means may comprise a telescoping connector between the first and second elongate members. The connecting means may comprise a sleeve having at least one lumen sized to slideably accommodate the first and second elongate members, the distal end of the first elongate member having a stop positioned distal to the at least one lumen and sized to prevent the distal end of the first elongate member from being withdrawn from the at least one lumen, the second elongate member having a stop positioned proximal to the at least one lumen and sized to prevent the proximal end of the second elongate member from being withdrawn from the at least one lumen. The functional element may comprise a filter, and the filter may have a body defining a proximally facing opening when in the expanded deployed configuration. The functional element may comprise an inflatable balloon or a body defining an interior cavity. A sleeve may be contained within the interior cavity. The connecting means also may comprise a first eyelet at the distal end of the first elongate member and a second eyelet at the proximal end of the second elongate member, the first eyelet forming a first loop which encircles the second elongate member and the second eyelet forming a second loop which encircles the first elongate member.

The functional element may include a proximal end connected to the second elongate member and a distal end connected to a distal slider which is slideable over the second elongate member, and further may include a loop at the distal end of the first elongate member which encircles the second elongate member between the proximal end of the functional element and the distal slider. The loop may be contained within the interior cavity. The connecting means may comprise the first elongate member having a tubular body having a lumen with an interior diameter and the second elongate member having a first region with an exterior diameter less than the interior diameter of the lumen of the tubular body, the first region being slideably received in the lumen of the tubular body. The second elongate member may have enlarged portions adjacent proximal and distal ends of the first region, which have an exterior diameter larger than the interior diameter of the lumen of the tubular body. At the first relative position, a first surface of the first elongate member can abut against a first surface of the second elongate member. This may further include means for gradually increasing resistance to movement between the first elongate member and the second elongate member as the first surface of the first elongate member is moved toward the first surface of the second elongate member.

The device may further comprise means for moveably connecting the filter and the first elongate member over a range of motion from a first position when the connecting means is in a relaxed state to a second position when the connecting means is in an expanded state such that resistance to movement between the filter and the first elongate member increases over the range of motion as the second position is approached. There also may be a means for locking the first elongate member to the second elongate member, the locking means having a locked position where the relative positions of the first and second elongate members are locked and an unlocked position where the first elongate member can be moved over the range of motion from the first relative position to the second relative position without resulting in movement of the second elongate member.

In a second embodiment, this invention is a distal protection device for use in a body lumen comprising a first elongate member having distal and proximal ends, a distal portion of the first elongate member having a lumen; a second elongate member having a distal end and an enlarged proximal end, the lumen of the distal portion of the first elongate member being sized to slideably receive a proximal portion of the second elongate member and having a constricted portion defining an opening which is smaller than the enlarged proximal end of the second elongate member such that the second elongate member is slideably retained in the lumen of the first elongate member; and a functional element carried by the second elongate element, the functional element being expandable from a delivery configuration to an expanded deployed configuration when the functional element is deployed in the body lumen.

In a third embodiment, this invention is a distal protection device for use in a body lumen comprising a first elongate member having distal and proximal ends; a second elongate member having distal and proximal ends; a functional element carried by the second elongate element, the functional element being expandable from a delivery configuration to an expanded deployed configuration when the functional element is deployed in the body lumen; and a sleeve having at least one lumen sized to slideably accommodate the first and second elongate members, the distal end of the first elongate member having a stop positioned distal to the at least one lumen and sized to prevent the distal end of the first elongate member from being withdrawn proximally from the at least one lumen, the second elongate member having a stop positioned proximal to the at least one lumen and sized to prevent the proximal end of the second elongate member from being withdrawn distally from the at least one lumen.

In a fourth embodiment, this invention is a distal protection device for use in a body lumen comprising a first elongate member having distal and proximal ends; a second elongate member having distal and proximal ends; a functional element carried by the second elongate element, the functional element being expandable from a delivery configuration to an expanded deployed configuration when the functional element is deployed in the body lumen; and a first eyelet at the distal end of the first elongate member and a second eyelet at the proximal end of the second elongate member, the first eyelet forming a first loop which encircles the second elongate member and the second eyelet forming a second loop which encircles the first elongate member.

In a fifth embodiment, this invention is a distal protection device for use in a body lumen comprising a first elongate member having distal and proximal ends; a second elongate member having distal and proximal ends; a functional element carried by the second elongate element, the functional element being expandable from a delivery configuration to an expanded deployed configuration when the functional element is deployed in the body lumen, the functional element having a proximal end which is connected to the second elongate member and a distal end connected to a distal slider which is slideable over the second elongate member; and a loop positioned at the distal end of the first elongate member which encircles the second elongate member between the proximal end of the functional element and the distal slider.

In a sixth embodiment, this invention is a distal protection device for use in a body lumen comprising a first elongate member having distal and proximal ends and having a tubular body having a lumen with an exterior diameter; a second elongate member having distal and proximal ends and having a first region with an exterior diameter less that the interior diameter of the lumen of the tubular body, the first region being slideably received in the lumen of the tubular body; and a functional element carried by the second elongate element, the functional element being expandable from a delivery configuration to an expanded deployed configuration when the functional element is deployed in the body lumen.

In a seventh embodiment, this invention is a method of occluding blood flow through the lumen of a vessel during a percutaneous procedure performed with a treatment device at a treatment site in the vessel comprising providing a distal protection device including a guidewire having first and second elongate members and an occlusive device carried by the second elongate member, the occlusive device being expandable from a delivery configuration to a deployed configuration, the first elongate member being connected to the second elongate member in a manner that permits the first elongate member to be moved with respect to the second elongate member over a range of motion without moving the second elongate member; introducing the guidewire and the occlusive device in its delivery configuration into the lumen of the vessel; advancing the guidewire through the vessel until the occlusive device is positioned at a desired location distal to the treatment site, at least a proximal portion of the first elongate member extending outside of the vessel; expanding the occlusive device to its deployed configuration to occlude the lumen of the vessel; advancing the treatment device over the guidewire to the treatment site while holding the first elongate member; and performing the percutaneous procedure at the treatment site with the treatment device while the lumen of the vessel is occluded.

In an eighth embodiment, this invention is a distal protection device for use in a body lumen comprising an elongate member having distal and proximal ends and having at least one longitudinal groove having distal and proximal ends; and a functional element carried by the elongate member, the functional element being expandable from a delivery configuration to an expanded deployed configuration when the functional element is deployed in the body lumen, the functional element having at least one projection sized to be accommodated within the groove and configured to be slideable within the groove between the distal and proximal ends of the groove.

In a ninth embodiment, this invention is a method of making a guidewire system for delivery of a functional element to a desired location in a body lumen comprising providing a first elongate member, a second elongate member and a functional element; mounting the functional element on the second elongate member; and connecting the first elongate member to the second elongate member in a manner that permits the first elongate member to be moved with respect to the second elongate member without moving the second elongate member.

In a tenth embodiment, this invention is a method of filtering emboli from blood flowing through the lumen of a vessel during a percutaneous procedure performed with a treatment device at a treatment site in the vessel comprising providing a distal protection device including a guidewire having first and second elongate members and a filter carried by the second elongate member, the filter being expandable from a delivery configuration when the filter is restrained to an expanded deployed configuration when the filter is unrestrained, the first elongate member being connected to the second elongate member in a manner that permits the first elongate member to be moved with respect to the second elongate member over a range of motion without moving the second elongate member; introducing the guidewire and filter in its delivery configuration into the lumen of the vessel; advancing the guidewire through the vessel until the filter is positioned at a desired location distal to the treatment site, at least a proximal portion of the first elongate member extending outside of the vessel; removing the restraint on the filter to expand the filter within the lumen of the vessel to its expanded deployed configuration; advancing the treatment device over the guidewire to the treatment site while holding the first elongate member; performing the percutaneous procedure at the treatment site with the treatment device; and filtering emboli from blood during the percutaneous procedure with the filter.

In an eleventh embodiment, this invention is a distal protection device for use in a body lumen comprising an elongate member having distal and proximal ends and at least one stop spaced proximally of the distal end; a functional element having a first slider disposed for translation along the elongate member between the stop and proximal end, the stop limiting translation of the slider in a distal direction; and means for gradually increasing the resistance between the slider and stop as the stop is moved proximally toward the slider.

The functional element may comprise a second slider disposed for translation along the elongate member between the stop and distal end, the stop limiting translation of the second slider in a proximal direction and wherein the means for increasing resistance includes means for gradually increasing the resistance between the second slider and the stop as the stop is moved distally toward the second slider. The means for increasing resistance may include a spring, an elastomeric tube, or first and second magnets having like-magnetic facing poles.

In a twelfth embodiment, this invention is a distal protection device for use in a body lumen comprising a first elongate member having distal and proximal ends; a second elongate member having distal and proximal ends; a functional element carried by the second elongate element, the functional element being expandable from a delivery configuration to an expanded deployed configuration when the functional element is deployed in the body lumen; and means for moveably connecting the filter and the first elongate member over a range of motion from a first relative position when the connecting means is in a relaxed state to a second relative position when the connecting means is in an expanded state such that resistance to movement between the filter and the first elongate member increases over the range of motion as the second relative position is approached.

In a thirteenth embodiment, this invention is a distal protection device for use in a body lumen comprising a first elongate member having distal and proximal ends; a second elongate member having distal and proximal ends; a functional element carried by the second elongate element, the functional element being expandable from a delivery configuration to an expanded deployed configuration when the functional element is deployed in the body lumen; and means for locking the first elongate member to the second elongate member, the locking means having a locked position where the relative positions of the first and second elongate members are locked and an unlocked position where the first elongate member can be moved over a range of motion from a first relative position to a second relative position without resulting in movement of the second elongate member.

In a fourteenth embodiment, this invention is a method of filtering emboli from blood flowing through the lumen of a vessel during a percutaneous procedure performed with a treatment device at a treatment site in the vessel comprising providing a distal protection device including a guidewire having first and second elongate members and a filter carried by the second elongate member, the filter being expandable from a delivery configuration when the filter is restrained to an expanded deployed configuration when the filter is unrestrained; locking the first elongate member to the second elongate member so that their relative positions are fixed; introducing the guidewire and filter in its delivery configuration into the lumen of the vessel; advancing the guidewire through the vessel until the filter is positioned at a desired location distal to the treatment site; removing the restraint on the filter to expand the filter within the lumen of the vessel to its expanded deployed configuration; unlocking the first elongate member from the second elongate member so that the first elongate member is moveable with respect to the second elongate member over a range of motion from a first relative position to a second relative position without resulting in movement of the second elongate member; advancing the treatment device over the guidewire to the treatment site after the first elongate member has been unlocked from the second elongate member; performing the percutaneous procedure at the treatment site with the treatment device; and filtering emboli from blood during the percutaneous procedure with the filter.

In a fifteenth embodiment, this invention is a method of occluding blood flow through the lumen of a vessel during a percutaneous procedure performed with a treatment device at a treatment site in the vessel comprising providing a distal protection device including a guidewire having first and second elongate members and an occlusive device carried by the second elongate member, the occlusive device being expandable from a delivery configuration to an expanded deployed configuration; locking the first elongate member to the second elongate member so that their relative positions are fixed; introducing the guidewire and occlusive device in its delivery configuration into the lumen of the vessel; advancing the guidewire through the vessel until the occlusive device is positioned at a desired location distal to the treatment site; expanding the occlusive device to its expanded deployed configuration to occlude the lumen of the vessel; unlocking the first elongate member from the second elongate member so that the first elongate member is moveable with respect to the second elongate member over a range of motion from a first relative position to a second relative position without resulting in movement of the second elongate member; advancing the treatment device over the guidewire to the treatment site after the first elongate member has been unlocked from the second elongate member; and performing the percutaneous procedure at the treatment site with the treatment device while the lumen of the vessel is occluded.

DETAILED DESCRIPTION OF THE PREFERRED EMBODIMENTS

Figure 1:
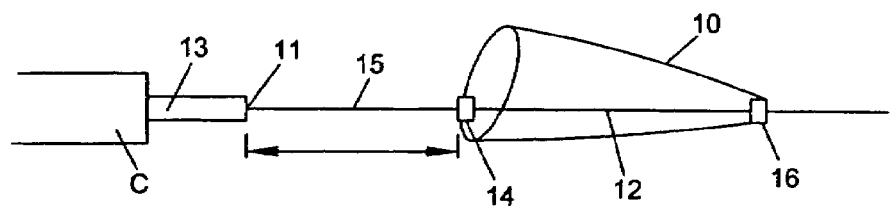
FIGS. 1 to 4 are schematic views of various embodiments of the distal protection device of this invention illustrating features which allow for the guidewire to be moved independently of the functional element.

Various embodiments of the invention are disclosed herein. Some of the embodiments are directed to devices that allow independent movement of the guidewire with respect to the filter or other functional element once the functional element has been deployed. (FIGS. 1-14). Other embodiments are directed to devices having a braking feature. (FIGS. 15-18). Brakes provide a means to cushion the force when a wire, moving with very low friction relative to a filter, encounters a stop. The brake provides tactile feedback that the hard stop is approaching, and this tactile feedback allows the doctor to adjust the motion accordingly. Other embodiments include a shock absorbing feature. (FIGS. 19-27). Shock absorbers act as distance-accommodating springs that are not frictionally independent from the wire. Both allow feedback to the physician so the physician can avoid dislodging or disrupting the functional device by excessive movement of the guidewire carrying the device during a vascular procedure.

Still other embodiments incorporate a locking feature that can be engaged or disengaged. (FIGS. 28-36). When engaged, the relative position of the functional device and guidewire is locked to allow accurate positioning and deployment of the functional device and, if desired, retrieval of the device. When the locking feature is disengaged, the guidewire can be moved independently of the device to allow some movement of the guidewire during, for example, catheter exchanges over the guidewire without dislodging or disrupting the functional device.

The terms "distal" and "proximal" as used herein refer to the relative position of the guidewire, catheters, and distal protection system in a lumen. Thus, "proximal" refers to a location upstream from the "distal" position. That is, the flow of a body fluid, such as blood, moves from the proximal to the distal portions of the device of this invention.

The various embodiments of distal protection systems of this invention are meant to encompass the use of any functional device to be deployed in a lumen or vessel of a patient in a minimally invasive procedure. It is to be understood that the devices described and illustrated below, in which the motion of the distal protection device relative to a guidewire is controllable by various means, applies to occlusive devices, filtration devices, and any other functional device where it is useful to allow limited movement and/or tactile feedback between the device and a guidewire that carries the device. Many of the embodiments show the functional device in the form of a filter having a windsock type shape. (See FIGS. 1, 3-12, 15-17, 19-22, and 25-36). The construction, deployment and retrieval of such a filter is described, for example, in U.S. Pat. No. 6,325,815 (Ser. No. 09/400,159, Kusleika et al.), which is incorporated by reference herein in its entirety. Other of the embodiments show the filter as a cup shaped device which forms a proximally facing opening when expanded. The construction, deployment and retrieval of such a filter is described in WO 96/01591 (Mazzochi et al.), which is incorporated by reference herein in its entirety. In still another embodiment the functional element is an occlusive device shown as a balloon. (FIG. 14). It will be understood however, that other types of occlusive devices may be used. For example, the various filters shown herein could be made into occlusive devices if the filter mesh were coated with a polymer. Additionally, an occlusive device could be formed from any substantially rigid support frame coated with flexible occlusive material. The occlusive material may be sheets or films of polymer, urethane, silicon, latex, rubber, or thin films of an engineered polyurethane such as polyester or nylon. The thin films may be biaxially oriented. It will be appreciated that these functional devices shown in the various embodiments are merely illustrative and are not meant to limit the scope of the invention.

Typically the distal protection system is introduced into a blood vessel through an introducing catheter. Methods of introducing guidewires and catheters and the methods for the removal of such devices from vessels are well known in the art of endovascular procedures. In a typical procedure using the device of this invention, the guidewire, the functional element which can be a filter or occlusive device, and the means for controlling the movement of the functional element all are loaded into an introducing sheath or catheter and moved into the vessel to the treatment site. This is done typically by moving the introducing sheath or catheter along a first, or introduction guidewire, which was put in place as the first step of the procedure at the region of interest. The sheath or catheter is advanced over the guidewire to the region of interest, and the guidewire removed. Then the functional element on a wire is advanced down the catheter to the region of interest but within the catheter or sheath. The catheter is withdrawn to deploy (expand) the functional element at the region of interest. If the functional element is a filter, the filter captures emboli released during the procedure by the treatment device which has been advanced over the guidewire. When the procedure is complete, the filter is retracted to a reduced removal configuration and removed from the vessel along with the guidewire.

Alternatively, if the functional element is self-expanding, it may be preloaded into a catheter and held in place by means of the catheter and they are together advanced through the vessel to the region of interest without using an initial guidewire. If the functional element is not self-expanding, such as a balloon or other structure requiring activation to be expanded, then the functional element can be collapsed, advanced to the treatment site, and expanded without the use of a catheter. If the functional element is an occlusive device, during or after the conclusion of the procedure, aspiration through a lumen of a catheter is performed before flow is restored in the body lumen by contracting the occlusive device to its removal configuration.

Typical dimensions of a filter used in the devices of this invention range from 2 mm to 90 mm in length, and from about 1 mm to 2 mm in diameter before deployment, and about 2 mm to 30 mm in diameter after deployment. A typical guidewire is about 0.3 to 1.0 mm in diameter and ranges from 75 cm to 320 cm in length.

The distal protection device comprises biocompatible materials. Materials also may be surface treated to produce biocompatibility. The guidewire may be formed of any material of suitable dimension and functional characteristics, and generally comprises metal wire. Preferably the materials are partly or completely radiopaque. The guidewire may be solid or may be hollow over some or all of its length.

The material used to make the filter preferably is self expanding. This can be accomplished by using self-expanding materials. These materials include metals such as stainless steel, titanium and its alloys, cobalt-chromium-nickel-molybdenum-iron alloy (commercially available under the trade designation Elgiloy™), and engineered polymers such as liquid crystal polymers, polyetheretherketone (PEEK), polyimide, polyester, silk, and the like. A shape memory metal is particularly suitable for those applications when it is desired for an element, such as a filter, to assume a pre-determined three dimensional shape or for a guidewire to maintain a pre-determined curvature. A shape memory metal comprising nickel and titanium is commercially available under the trade designation "Nitinol" in various dimensions and is suitable for use as both a guidewire and a filter. For example, nitinol tubular braid can be heat set into a desired shape, compressed for delivery to a site, and then released to form the heat-set shape.

The filter may comprise any material that is suitably flexible and resilient, such as a mesh. The filter may comprise braided, knitted, woven, or non-woven fabrics. Non-woven fabrics may additionally be treated to fuse some or all of the fiber intersections. The fabric may be electrospun. Suitable material includes that formed from sheets or films, polymeric or metallic, with holes formed by mechanical means such as laser drilling and punching, or by chemical means such as selective dissolution of one or more components. For example, a suitable filter material is braided tubular fabric comprising nitinol shape memory metal. Mesh fabric of nitinol material can be heat-set to a desired shape in its expanded configuration. The filter material is preferably at least partially radiopaque. The filter material can be made radiopaque by plating, or by using core wires, tracer wires, or fillers that have good X-ray absorption characteristics compared to the human body.

In some embodiments of the filter, fixed or slideable elements at the ends of the filter are discussed. These slideable elements may comprise inner and outer annular rings. (Not shown in the FIGS.). The first ring fits within the second ring. The inner diameter of the first ring is larger than the diameter of the guidewire so that the sliding element can slide over the guidewire. The sliding element can be affixed to the filter fabric by placing the fabric between the first and second rings. However, this is not meant to be limiting, and the fabric can also be affixed to the slideable element by adhesive, solder, crimping, or other means known in the art. The slider may comprise any stiff material such as metal or polymer and preferably the slider is radiopaque. Suitable materials include stainless steel, titanium, platinum, platinum/iridium alloy, gold alloy, polyimide, polyester, polyetheretherketone (PEEK), and the like.

By "fixed element" is meant an element that is attached to the guidewire and does not move independently of it. The fixed element may be an annular ring but also included within this meaning is an element that is crimped, adhered, soldered, or otherwise fastened directly to the guidewire. In any event, the sliding or fixed elements typically comprise radiopaque material to assist in the placement of the filter.

Movement of a sliding element with respect to the guidewire can be facilitated by coating one or both of the inside of the sliding element and the outside of the guidewire with a friction-reducing coating, such as polytetrafluoroethylene (commercially available under the trade designation Teflon™) or a lubricious hydrophilic coating.

Spring elements disclosed in some of the embodiments are composed of metal, polymer, or combination of the two. Suitable materials include stainless steel, Nitinol, spring steel, Elgiloy, polyimide, PEEK, oriented polymer filaments, metal reinforced polymers, rubbers, polyurethanes, silicones, and the like.

Some embodiments include a "floppy tip" at the distal end of the device. The floppy tip provides an atraumatic and radiopaque terminus for the device. An atraumatic tip prevents vessel injury during initial placement or subsequent advancement of the device. A radiopaque tip helps the physician verify suitable tip placement during fluoroscopy. The floppy tip preferably comprises a springy or resilient material, such as a metal (e.g., stainless steel, iron alloys such as Elgiloy™, and shape memory metal such as Nitinol) or polymer (e.g., polyetheretherketone (PEEK), polyimide, polyester, polytetrafluoroethylene (PTFE), and the like). Springy materials are desirable because they tend to retain their shape. The physician will initially 'shape' the tip, typically with a slight curve, and then as the wire is advanced through the body the tip will be deflected as it encounters obstacles. It is desirable, after the inevitable deflections during insertion, that the tip restore itself to the pre set shape. Polymeric materials additionally may be reinforced with metals or other fillers. The material may be a monofilament or multifilament (such as a cable). The floppy tip may be tapered or have a uniform diameter over its length. The floppy tip could comprise a tube, or could have circular, flat, or other cross-sections. It could be coiled. The tip could comprise one or more elements (i.e., parallel independent structures). The tip may be polymer-coated or otherwise treated to make the surface slippery. The floppy tip can be any desired length.

Other elements of the filtration device also comprise biocompatible materials, and these include metals and polymeric materials. These materials can be treated to impart biocompatibility by various surface treatments, as known in the art. When wire is used, the wire is selected on the basis of the characteristic desired, i.e., stiffness or flexibility, and the properties can depend upon both the diameter of the wire and its cross-sectional shape. The size, thickness and composition of elastic materials are selected for their ability to perform as desired as well as their biocompatibility. It is to be understood that these design elements are all within the scope of this invention.

The various embodiments of the invention will now be described in connection with the drawing figures. It should be understood that for purposes of better describing the invention, the drawings have not been made to scale. Further, some of the figures include enlarged or distorted portions for the purpose of showing features that would not otherwise be apparent.

Wire Motion

FIGS. 1-14 illustrate embodiments in which there is independent motion allowed between the filter and an elongate guide member such as a guidewire. This can be done by various sliding interlocking wire arrangements, tethers with overlying slideable tube arrangements, and the like. The independent wire motion permits the wire to move without disturbing filter position, and this carries all of the advantages described above.

FIG. 1 is a schematic view of filter 10, proximal element 14, and distal slider element 16 disposed about a first guidewire 12. Proximal element 14 is attached to flexible wire 15 (preferably having a narrow diameter), which itself is crimped or by other means attached to second guidewire 13 at region 11. Guidewire 13 is shown emerging from the distal end of catheter C. Catheter C is shown generically and may be a delivery catheter and/or a retrieval catheter. Catheter C is shown only in FIG. 1 and is not repeated in the other drawing figures since it will be appreciated that a catheter is used to deliver and retrieve the embodiments disclosed herein. For purposes of clarity, the filter 10 and the other filter and device embodiments disclosed herein are shown only in outline so that other details of the invention are more easily understood. The length of flexible wire 15 between the distal end of guidewire 13 and the fixed proximal element 14 permits movement of guidewire 13 (indicated by the arrows) without causing axial movement of the filter. Further, because of the flexibility of the tether, wire bias is decoupled from the filter, leading to excellent radial independence of filter position relative to wire motion.

Figure 2:
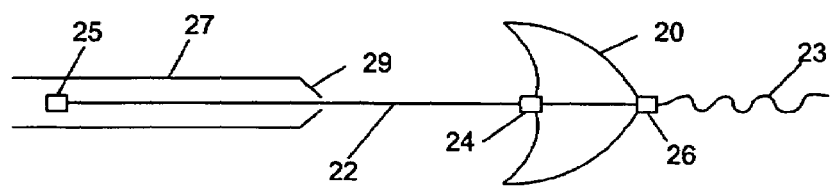

FIG. 2 is a schematic view of filter 20, proximal element 24, and distal slider element 26 disposed about guidewire 22. The guidewire ends distally at floppy tip 23. Floppy tip 23 is provided as an atraumatic and radiopaque terminus for the filter. The tip comprises any suitably flexible and springy material, as discussed above. Wire 22 extends proximally to stop 25 which is configured to fit within the core of hollow guidewire 27. Guidewire 27 may be hollow along its entire length or only along a distal portion sufficient to accommodate wire 22. Restriction 29 at the distal end of this hollow wire provides a stopping mechanism for movement of the filter. Once filter 20 is deployed within a vessel, guidewire 27 may be moved independently of filter 20 by an amount limited only by the distance between stop 25 and proximal element 24.

Figure 3:
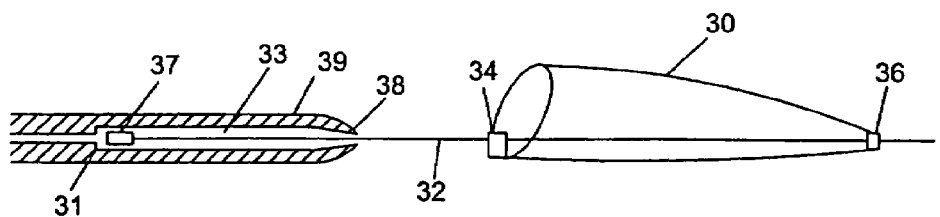

FIG. 3 is a schematic view of a filter 30, proximal fixed element 34, and distal slider element 36 disposed about wire 32. Wire 32 has an enlarged proximal end 37. Hollow guidewire 39 (shown in cross section as indicated by cross hatching) contains recess 33, which slideably receives a proximal portion of wire 32 including enlarged end 37. Hollow guidewire 39 has restriction 38 at its distal end to prevent enlarged end 37 from exiting recess 33. Restriction 38 is sized to allow sliding motion of the proximal portion of wire 32. Hollow guidewire 39 also contains step 31 at the proximal end of recess 33 to limit the proximal movement of enlarged end 37. Hollow guidewire 39 may be hollow over its entire length or may be hollow over only the distal portion including restriction 38 and step 31. Once filter 30 is deployed within a vessel, guidewire 39 may be moved independently of filter 30 by an amount limited only by the distance between step 31 and restriction 38.

Figure 4:
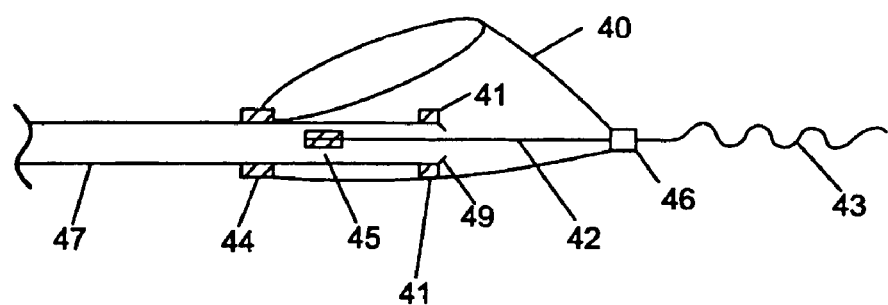

FIG. 4 is a schematic view of an embodiment similar to that shown in FIG. 2. Filter 40 and distal fixed element 46 are disposed about wire 42. Wire 42 ends distally at floppy tip 43. Wire 42 extends proximally to stop 45 configured to fit within the core of hollow guidewire 47. Proximal slider element 44 (shown in cross section as indicated by cross hatching) is disposed about hollow guidewire 47. Guidewire 47 extends into the filter. Restriction 49 at the distal end of guidewire 47 provides a stopping mechanism to ensure that stop 45 is retained within guidewire 47. In this embodiment, guidewire 47 may move independently of the filter by an amount equal to the distance between stop 45 and distal element 46. Filter length may be longer than the length of independent wire motion. Alternatively filter length can be shorter than the length of independent wire motion by suitable tapering of restriction 49 to allow for unimpeded motion of slider 44 over restriction 49. Alternatively, optional stop 41 (shown in cross section as indicated by cross hatching) may be added to limit the distal axial motion of proximal slider element 44.

Figure 5:
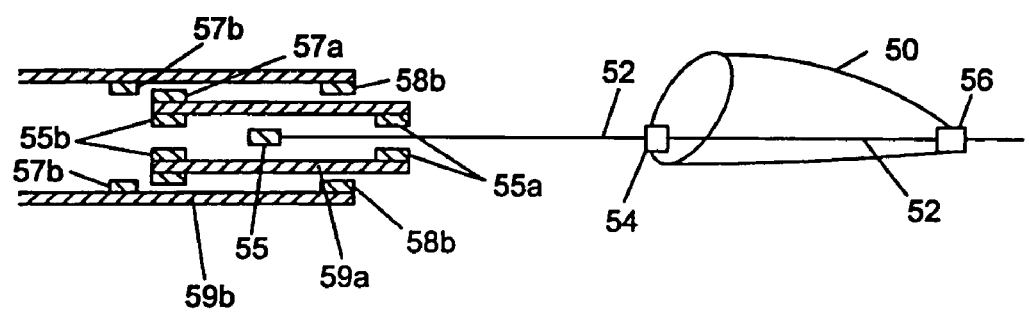
FIG. 5 is a schematic view of a further embodiment wherein the guidewire is provided with a telescoping structure allowing it to move independently of the functional element.

FIG. 5 is a schematic view of filter 50, proximal fixed element 54, and distal slider element 56 disposed about wire 52. Wire 52 extends proximally through one or more hollow guidewires. Two guidewires, shown here as 59a and 59b, are illustrated in the figure and are shown in cross section as indicated by cross hatching. Wire 52 is provided with proximal retaining element 55. Hollow guidewires 59a and 59b have proximal retaining elements 57a and 57b, respectively, and distal retaining elements 58a and 58b, respectively. These retaining elements may be a continuous annular projection disposed on the hollow guidewires, as shown, or they may be discontinuous. Hollow guidewires 59a and 59b slideably cooperate in a telescoping fashion, with the retaining elements 57(a and b) and 58b serving to limit the relative motion of these wires. The motion of proximal retaining element 55 on wire 52 is restrained by retaining elements 55a and 55b on the inside of hollow guidewire 59a. The hollow guidewire optionally could be tapered at its distal end (i.e., nearer the filter), similar to the taper shown in the embodiment of FIG. 3. This device permits movement of the guidewire while the filter remains stationary a distance equal to the distance between retaining element 55 and proximal element 54 plus the distance between proximal retaining element 57b and distal retaining element 58b.

Figure 6A:
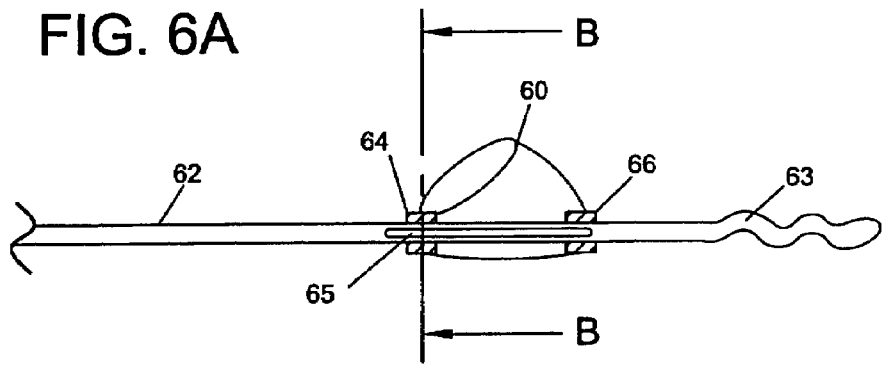
FIG. 6A is a schematic view of an alternate embodiment of the device of this invention having a slotted guidewire and FIG. 6B is a cross-sectional view along line B-B of FIG. 6A.
Figure 6B:
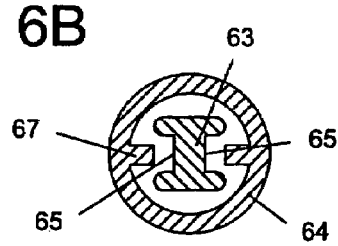

FIG. 6A is a schematic view of filter 60, proximal slider element 64, distal slider element 66, disposed about guidewire 62 having floppy distal tip 63. The drawing shows the slider elements in cross-section (as indicated by crosshatching), disposed about guidewire 62, whose scale is exaggerated for this drawing. Guidewire 62 may be hollow or solid and has one or more longitudinal grooves or slots (slot 65 is shown) that slideably receive tangs 67 emanating from the internal diameter of either slider element or both. In the embodiment of FIG. 6A, the tangs extend from slider 64. FIG. 6B shows a cross-section along line B-B of slider element 64 having tangs 67 engaging two slots 65 in guidewire 62. Thus the motion of the filter along the guidewire is controlled by the length of slot 65 and the movement of slider element 64 in cooperation with it.

Figure 7A:
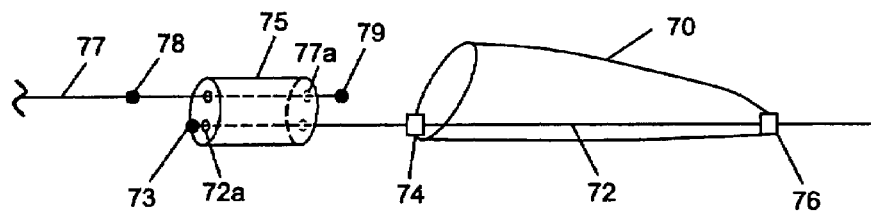
FIG. 7A is a further embodiment having first and second guidewires in a sleeve.

FIG. 7A is a schematic view of filter 70, proximal fixed element 74, and distal slider element 76 disposed about first guidewire 72. Guidewire 72 extends proximally to proximal stop 73 through sleeve 75. Sleeve 75 may comprise metal or polymeric material and may be cylindrical or may have chamfered ends. Second, interlocking guidewire 77 with optional stop 78 extends through the sleeve from the proximal direction to distal stop 79. Guidewires 72 and 77 extend through sleeve 75 through one or more lumens sized to accommodate the guidewires but to block passage of stops 73, 78, and 79 and proximal fixed element 74. Specifically, in FIG. 7A, sleeve 75 has lumens 72a and 77b to accommodate guidewires 72 and 77, respectively. In this embodiment, guidewire 77 can move independently of filter 70 by an amount equal to the distance between stops 78 and 79 less the length of the sleeve plus the distance between stop 73 and proximal element 74 less the length of the sleeve.

Figure 7B:
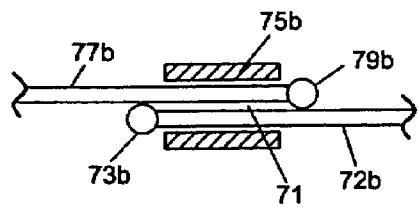
FIGS. 7B and 7C are detail views of two additional embodiments.
Figure 7C:
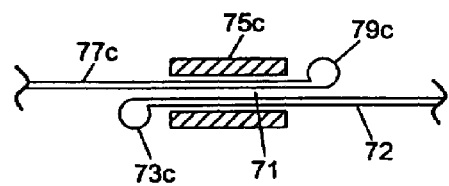

FIGS. 7B and 7C show partial detail cross sectional views of the sleeve portion. A single lumen 71 accommodates both guidewires. In FIG. 7B, the rounded balls that form stops 73 and 79 are aligned with the axis of the guidewires, while in FIG. 7C, they are offset to facilitate clearance and movement of the guidewires through the lumen. In FIG. 7B, guidewire 72b extends through sleeve 75b to stop 73b; guidewire 77b extends through sleeve 75b to stop 79b. Similarly, FIG. 7C shows guidewire 72c extending through sleeve 75c to stop 73c and guidewire 77c extending through sleeve 75c to stop 79c.

Figure 8A:
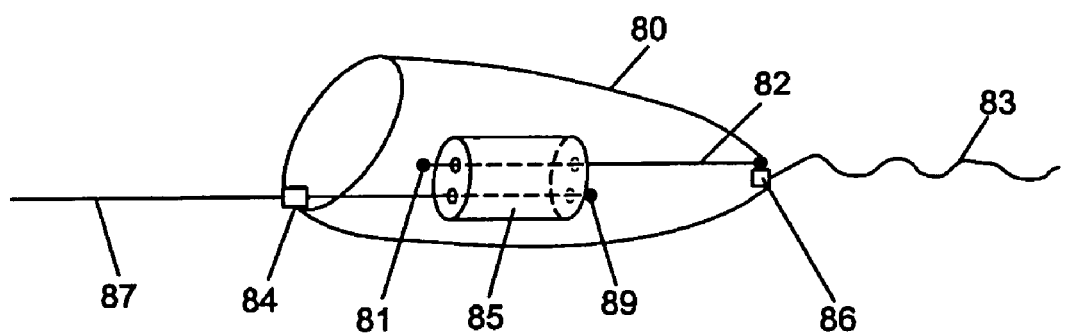
FIG. 8A is a schematic view of an alternate embodiment having first and second guidewires in a sleeve within the filter.
Figure 8B:
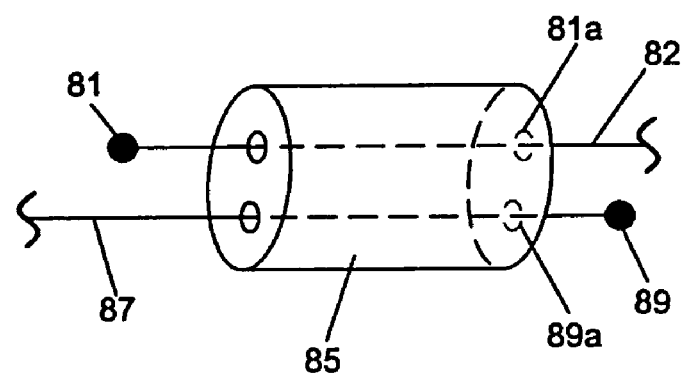
FIG. 8B is a detail view of FIG. 8A.

FIGS. 8A and 8B show an embodiment similar to FIG. 7A, wherein the guidewires pass through a sleeve which is located inside the filter. Filter 80 and proximal slider element 84 are disposed about first guidewire 87. Filter 80 and distal slider element 86 are disposed about second guidewire 82. Guidewire 87 extends from the proximal direction into the filter and terminates at stop 89. Guidewire 82 extends from the distal direction into the filter and terminates at stop 81. Guidewires 87 and 82 extend through sleeve 85, located within the filter, through one or more lumens (81a and 89a) sized to accommodate guidewires 82 and 87 but to block the passage of stops 81 and 89. In addition, guidewire 82 terminates at floppy tip 83 at its distal end. Sleeve 85 helps to stabilize and control motion of the two guidewires with respect to one another. This embodiment allows for independent motion of guidewire 87 with respect to filter 80 in a manner similar to that described with respect to FIG. 7A.

Figure 9:
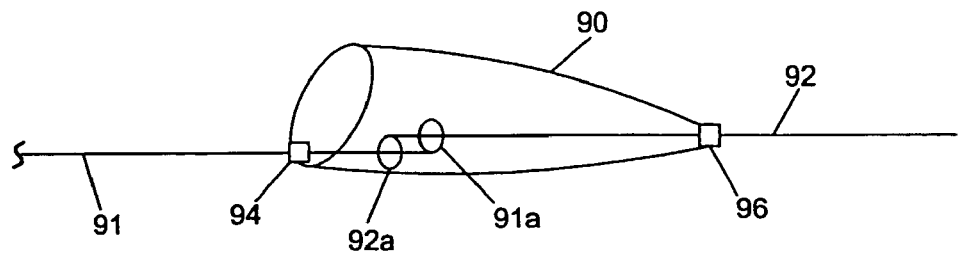
FIGS. 9, 10A, and 10B are schematic views of alternate embodiments of the device of this invention wherein independent movement of the guidewire is provided by various eyelet arrangements.

FIG. 9 is a schematic view of an interlocking eyelet arrangement. This embodiment has filter 90, proximal slider element 94, and distal slider element 96 disposed about proximal guidewire 91 having interlocking eyelet 91a and distal guidewire 92 having interlocking eyelet 92a. Eyelet 91a is disposed about guidewire 92 and eyelet 92a is disposed about guidewire 91. In addition, this embodiment is equally functional if slider element 96 is fixed. Independent wire motion is achieved by the eyelets sliding over the wires while the wire(s) slide through the slider element(s).

Figure 10A:
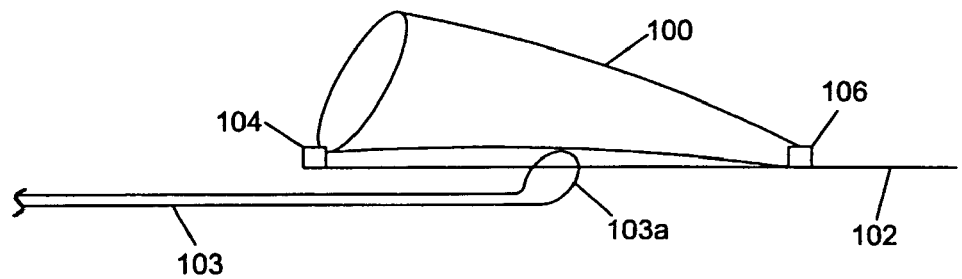
Figure 10B:
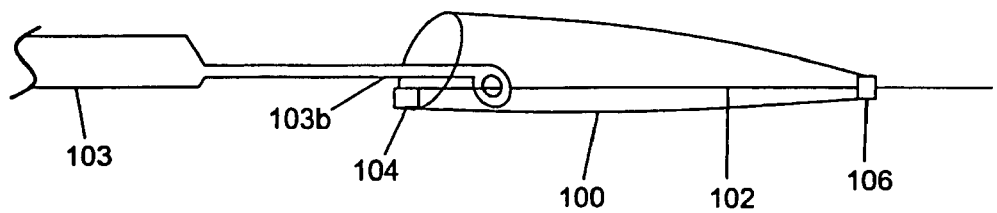

FIG. 10A illustrates a filtration device in which a snare loop 103a, at the distal end of first guidewire 103, loops around a second guidewire 102. Snare loops can be built according to the methods disclosed in U.S. Pat. No. 5,171,233 (Amplatz et al.). In FIG. 10A, proximal fixed element 104 and distal slider element 106 are disposed about guidewire 102. Filter element 100 is disposed beside guidewire 102. Snare loop 103a passes around guidewire 102 but does not pass through filter 100. In FIG. 10B, filter 100, proximal fixed element 104 and distal slider element 106 are disposed about second guidewire 102, and first guidewire 103 has snare loop 103b at its distal end. FIG. 10A illustrates snare loop 103a outside filter 100 and FIG. 10B illustrates snare loop 103b within filter 100. In either embodiment, the loop can move between the fixed proximal element and the distal sliding element to allow independent movement of guidewire 103 with respect to filter 100 in that amount.

Figure 11:
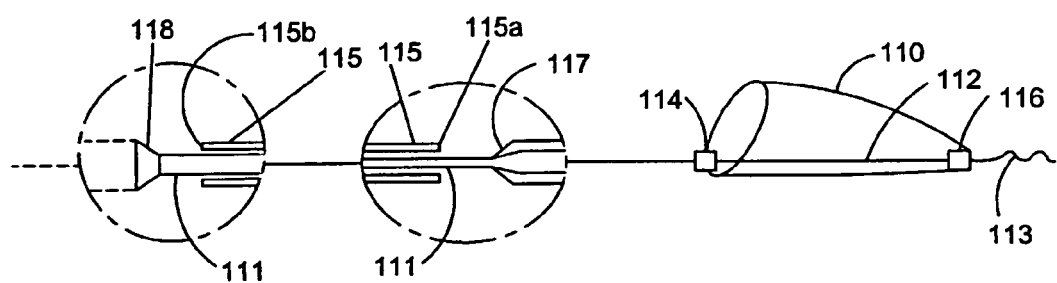
FIGS. 11, 12, 13A, 13B, and 13C are schematic views and partial cross-sectional views of alternate embodiments of the device of this invention where independent guidewire movement is provided by movement of a first completely or partially hollow guidewire with respect to a second guidewire upon which the functional device is mounted.

FIG. 11 illustrates a schematic view and partial cross-sectional views of a filter 110, proximal fixed element 114, and distal slider element 116 disposed about guidewire 112, which ends distally at floppy tip 113. Enlarged partial cross-sectional views show the shape of guidewire 112 as it extends proximally through a second guidewire, which comprises hypotube 115. Guidewire 112 has a reduced diameter 111, which is slideably received within hypotube 115, and an enlarged end 118. Enlarged end may be only a few millimeters in length or optionally could be 100 cm long or more. Distal motion of hypotube 115 relative to guidewire 112 is limited by impingement of hypotube 115 distal end 115a against step 117. Proximal motion of hypotube 115 relative to guidewire 112 is limited by impingement of proximal end 115b of hypotube 115 against enlarged end 118. Chamfers are preferably incorporated in both proximal and distal ends of hypotube 115, step 117, and proximal and distal ends of enlarged end 118 to provide for smooth passage of catheters and the like over the assembly. Preferably, the diameter of enlarged end 118, hypotube 115, and distal portion of guidewire 112 are approximately equal and sized to be compatible with and allow delivery of conventional catheters over hypotube 115. Guidewire 112 and hypotube 115 are sized so that when the filter element is deployed distally of a treatment site the hypotube extends from a location inside the patient to a location outside of the patient. Alternatively, the hypotube may be entirely outside the patient. This allows the physician when making exchanges to minimize filter movement while making the exchange. Any motion of hypotube 115 during the exchange is not passed on to guidewire 112 or filter 110 since hypotube 115 moves independently of both the guidewire and the filter. The embodiment of FIG. 11 has the advantage of providing for a very large amount of motion of hypotube 115 relative to filter 110. Specifically, when catheter exchanges are made over guidewire 112 during a procedure, hypotube 115 can move independently of guidewire 112/filter 110 by an amount equal to the distance between end 118 and step 117 less the length of hypotube 115.

Figure 12:
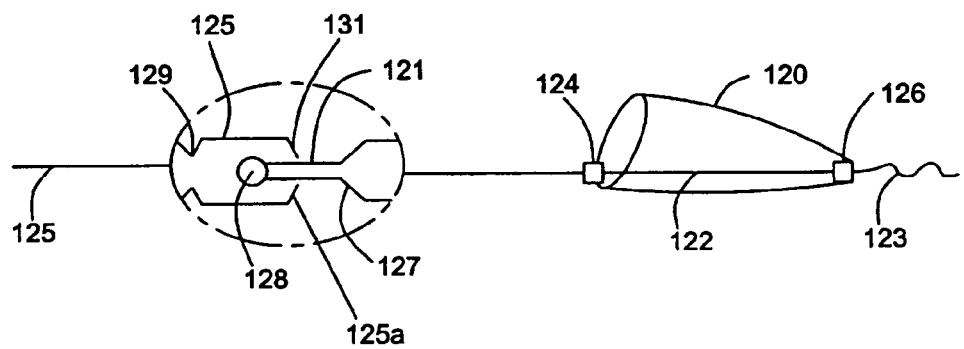

FIG. 12 illustrates a schematic view and enlarged partial cross-sectional view of filter 120, proximal fixed element 124, and distal slider element 126 disposed about guidewire 122, which ends distally at floppy tip 123. Partial cross-sectional views show the shape of guidewire 122 as it extends proximally through the distal end of a second guidewire comprising hypotube 125. Guidewire 122 has step 127, reduced diameter section 121, and enlarged proximal end 128. Hypotube 125 has crimp 129 and distal restriction 125a. Distal motion of hypotube 125 relative to wire 122 is limited by impingement of hypotube distal end 131 against step 127 or by impingement of crimp 129 against enlarged end 128. Proximal motion of hypotube 125 relative to guidewire 122 is limited by impingement of hypotube restriction 125a against enlarged end 128. Chamfers are preferably incorporated in proximal and distal ends of hypotube 125 and step 127 to provide for smooth passage of catheters and the like. Preferably the diameter of hypotube 125 and proximal portion of guidewire 122 are approximately equal and sized to be compatible with conventional catheters.

Figure 13A:
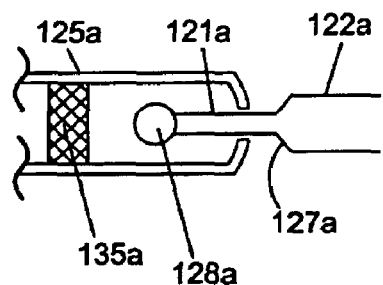
Figure 13B:
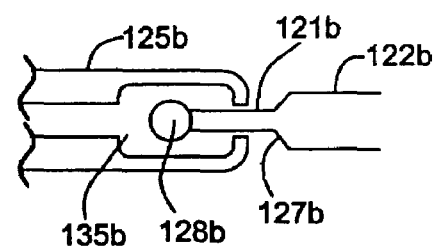
Figure 13C:
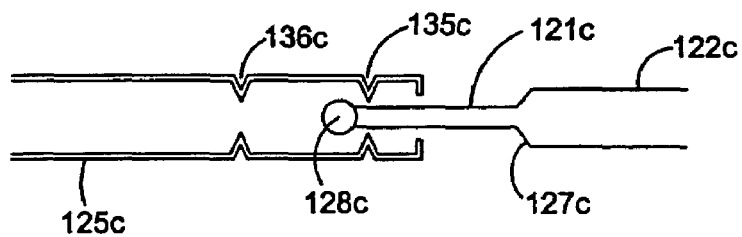

Alternative constructions of the embodiment of FIG. 12 are shown in FIGS. 13A to 13C, which illustrate partial cross-sectional views of the shape of guidewire 122 as it extends proximally into the distal end of hypotube 125. In FIG. 13A, guidewire 122a has step 127a, reduced diameter section 121a, and enlarged proximal end 128a. Hypotube 125a is joined to a solid piece of material 135a within the hypotube by means of soldering, welding, and the like. Material 135a serves to limit the distal movement of hypotube 125a with respect to guidewire 122a. In FIG. 13B, guidewire 122b has step 127b, reduced diameter 121b, and enlarged proximal end 128b. Hypotube 125b is provided with a counterbore resulting in proximal step 135b, which serves a function similar to material 135a in FIG. 13A. FIG. 13C illustrates guidewire 122c with step 127c, reduced diameter 121c, enlarged proximal end 128c, and two crimps 135c and 136c in hypotube 125c. These crimps serve to limit the range of guidewire motion to the region between the two crimps. This alternative construction differs from FIG. 12 in that the length of tube 125c distal to distal crimp is quite long so as to preserve axial alignment between tube 125c and wire 122c.

Figure 14A:
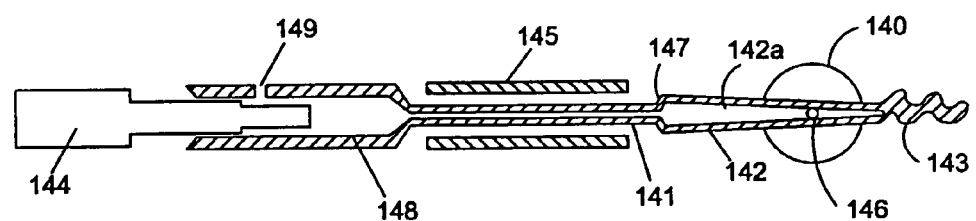
FIG. 14A is a schematic view of a device similar to the embodiment of FIG. 11 but where the functional element is a balloon and the guidewire is provided with a valve and an inflation lumen.

FIG. 14A is a schematic view of a balloon protection device which provides for relatively independent guidewire motion in the same manner as described for the embodiment of FIG. 11. The device is shown in cross section. Balloon 140 is attached to hollow guidewire 142 at the distal end of the guidewire; floppy tip 143 extends distally from guidewire 142, and balloon port 146 communicates between the guidewire lumen 142a and the interior of the balloon. Guidewire 142 has reduced diameter portion 141, step 147, and enlarged end 148 that serve to restrict the motion of slideably coupled hypotube 145.

Figure 14B:
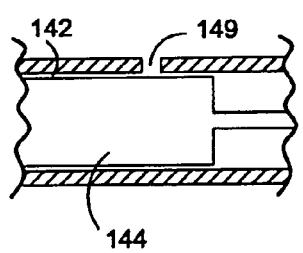
FIGS. 14B and 14C are partial cross-sectional views of the device of FIG. 14A.
Figure 14C:
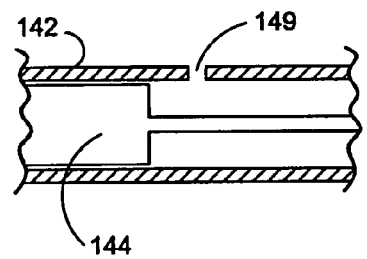

FIGS. 14B and 14C illustrate partial cross-sectional views of solid guidewire 144 within hollow guidewire 142. Solid guidewire 144 is manipulated in an axial direction to open and close port 149. The proximal end of hollow guidewire 142 communicates with port 149, which is in fluid communication with balloon 140 through balloon port 146. Proximal solid guidewire 144 is slideably received within proximal end of hollow wire 142 and extends proximally beyond proximal end of wire 142. When proximal solid guidewire 144 is retracted proximally relative to hollow guidewire 142, port 149 is opened to allow a fluid to be injected into port 149 causing balloon 140 to be inflated. When proximal solid guidewire 144 is advanced distally relative to hollow guidewire 142, the port is closed. Alternatively, port 149 can be located distal to hypotube 145. Alternatively, hypotube 145 can be slideably disposed on proximal solid wire 144. FIG. 14B shows that when the valve is closed, port 149 is occluded by solid guidewire 144. FIG. 14C shows the relative position of guidewires 142 and 144 when the valve is open; port 149 is not occluded.

Brakes

FIGS. 15 to 18 illustrate embodiments in which there is some form of braking feature included on the movement of the wire relative to the filter (and, thus, of movement of the filter). This braking feature may be accomplished by adding a compressible element or cooperating magnets along the guidewire within the filter, or by adding a brake either inside or outside of the filter to cooperate with any of the stops, distal restrictions, slot ends, or hypotube ends shown in the preceding figures. The brake permits increased levels of tactile feedback to the physician manipulating the guidewire. This tactile feedback enables the user to determine the range of guidewire movement with respect to the filter or other functional device carried by the guidewire. It should be understood that the various brake embodiments described herein may be incorporated into any of the previously described wire motion embodiments or into other known systems where there is a desire to limit the relative motion between a functional element carried on a guidewire.

Figure 15A:
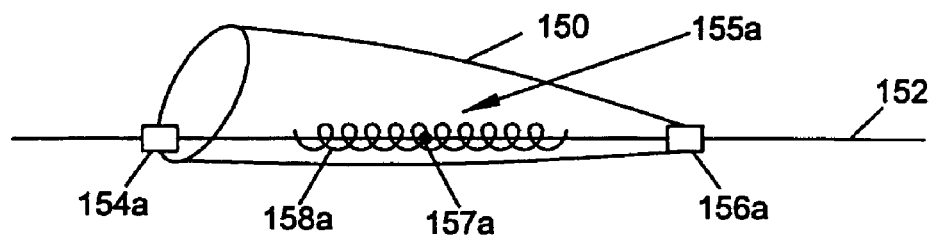
FIGS. 15A to 15C and 16 to 18 are schematic views of alternate embodiments of the distal protection device of this invention showing various brake configurations.

FIG. 15A is a schematic view of filter 150, guidewire 152, proximal slider element 154a, distal slider element 156a, and brake element 155a located within the filter. Brake element 155a comprises spring 158a fastened to guidewire 152 at connection point 157a. During the procedure, wire motion may occur caused, for example, by exchange of catheters over the guidewire. As the wire is advanced proximally or distally slider element 154a or 156a will contact an end of brake element 155a. The physician will sense a gradually increasing wire resistance as the brake element is compressed with increasing wire travel, and can use this sensation to avoid moving the wire excessively and thereby cause undesired movement of the filter. Brake element 155a may comprise metal or polymeric material.

Figure 15B:
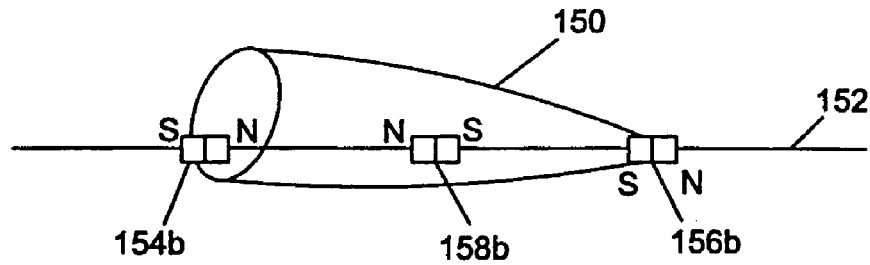

FIG. 15B is a schematic view of filter 150, guidewire 152, proximal slider element 154b comprising a magnet or to which a magnet is attached, distal slider element 156b comprising a magnet or to which a magnet is attached, and fixed element 158b comprising a magnet or to which a magnet is attached. Fixed element 158b is attached to guidewire 152 between the proximal and distal slider elements. The magnets are oriented such that a south pole of one slider magnet faces the south pole of the adjacent fixed magnet, and the north pole of the other slider magnet faces the north pole of the adjacent fixed magnet (as designated by N and S in the drawing). As slider elements 156b or 154b approach fixed element 158b, there is a gradually increasing repulsive force due to the repulsion of like magnetic poles. Thus, the sliders will tend not to make contact with the fixed element. The physician will sense a gradually increasing wire resistance as the magnets approach each other with increasing wire travel, and can use this sensation to avoid moving the wire excessively and thereby cause undesired motion of the filter.

Figure 15C:
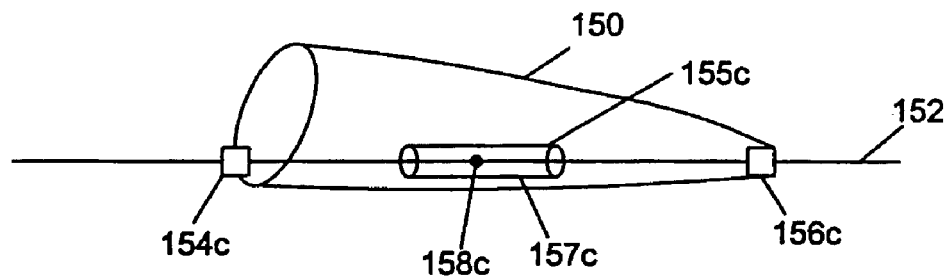

FIG. 15C is a schematic illustration of filter 150, guidewire 152, proximal slider element 154c, distal slider element 156c, and fixed element 155c located within the filter. Element 155c comprises an elastomeric sleeve 157c fused to guidewire 152 at connection point 158c. Either slider (154c or 156c) will contact an end of the sleeve, and the tubing will progressively brake the motion of the slider by compressing with gradually increasing force as the slider presses against it. The embodiment of FIG. 15C has many of the same advantages as those described for the embodiments of FIGS. 15A and 15B with respect to providing the physician with a sense of increasing resistance if there is excessive wire motion.

Figure 16:
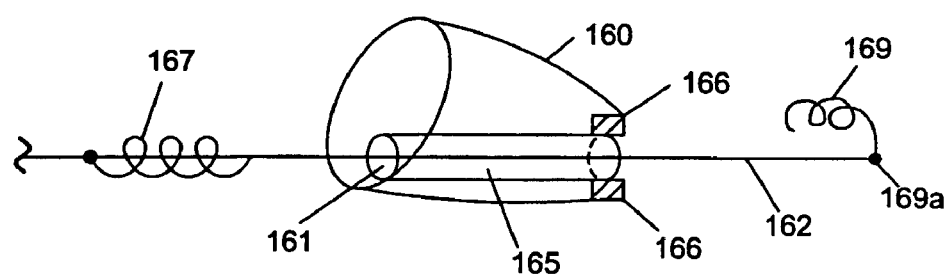
Figure 17:
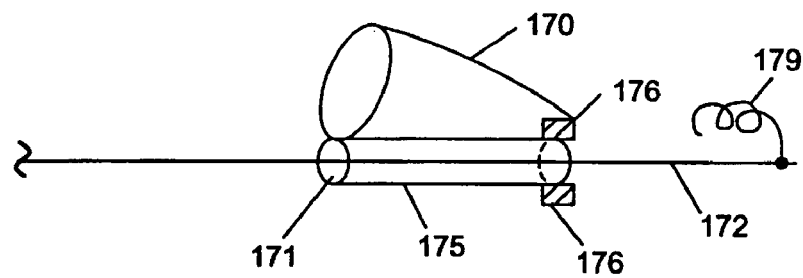

FIGS. 16 and 17 show embodiments incorporating a braking system, wherein respectively, a filter (160 and 170) is attached to a tube (165 and 175) having a lumen (161 and 171) which slidingly accommodates guidewire (162 and 172). The proximal end of the filter is fixed to the tube while the distal end of the filter is connected to a sliding element (166 and 176, illustrated in cross section, as indicated by the cross hatches) which slides over the tube. In FIG. 16, brakes 167 and 169 are positioned both distal and proximal of the tube on the guidewire. The brakes are shown as coil or spring elements of two different types. The same or different types could be used in one device. Brake 167 is a coil attached to and disposed about guidewire 162 and brake 169 is attached to the guidewire at point 169a. In FIG. 17, only a distal brake 179 is shown. It will be appreciated that braking arrangements as disclosed in FIGS. 15B and 15C are equally applicable to the embodiments of FIGS. 16 and 17.

Figure 18:
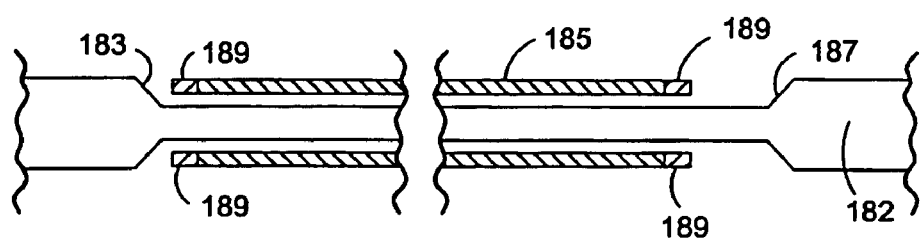

FIG. 18 is a partial cross-sectional view that shows brake principles similar to those discussed in connection with FIG. 15 to 17 but applied to wire motion permitting embodiments such as those described in FIG. 11 and FIG. 14. Hypotube 185 is disposed over wire 182 and is equipped with brake elements 189 at both the proximal and distal ends of proximal hypotube 185. Distal translation of hypotube 185 will result in progressive engagement of brake element 189 with step 187. Proximal motion of the hypotube 185 will similarly result in progressive engagement of the proximal brake 189 with enlarged end 183. Brake element 189 can be composed of a coil spring, an elastomer, a magnet (having a corresponding magnet on the opposing face, e.g., step 187), and other devices and materials that can function as a brake.

Brakes can be similarly applied to the embodiments shown in FIGS. 2 to 9, 10A and 10B, 12, and 13 by those of ordinary skill in the art. For example, brake elements can be applied to the distal end of stop 25 and proximal end of restriction 29 in FIG. 2. A tubular brake can be substituted for or applied to both ends of sleeve 75 in FIGS. 7A to 7C. A brake can be interspersed between the interlocking eyelets (92a and 91a) in FIG. 9 or between the snare loop (103a/103b) and proximal band 104 in FIG. 10A Shock Absorbers FIGS. 19 to 27 illustrate embodiments which incorporate a shock absorber feature. A shock absorber is used in embodiments where there is a physical connection between a functional device such as a filter and a guidewire. The physical connection limits relative movement between the filter and the guidewire. The shock absorber is incorporated into the physical connection to provide increasing resistance as the wire is moved with respect to the filter. The shock absorber feature provides tactile feedback to the physician concerning the extent of guidewire motion relative to the filter. The shock absorbers permit comparatively independent motion of the guidewire relative to the filter.

Figure 19:
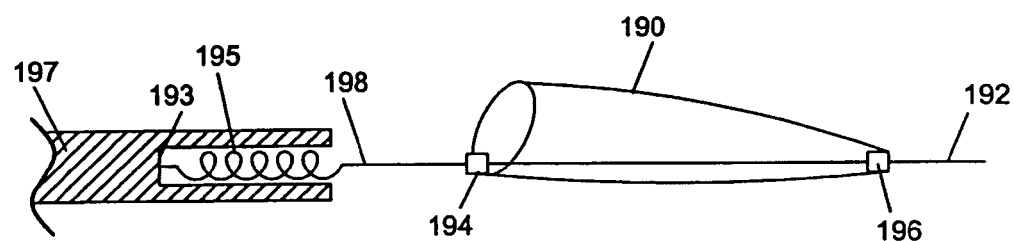
FIGS. 19 to 27 are schematic views of various alternate embodiments of the distal protection device of this invention equipped with a shock absorber feature.

FIG. 19 is a schematic illustration of a distal protection device comprising filter 190, proximal fixed element 194, and distal slider element 196 disposed about guidewire 192. Proximal fixed element 194 is attached to flexible tether 198. Tether 198 is attached at its proximal end to a shock absorber comprising a spring element 195 which itself is attached within a hollow core 193 of a second (host) guidewire 197 (shown in cross section, as indicated by cross hatching). In use the spring element 195 manages the tether 198 so that excess tether is withdrawn into hollow core 193 of the second guidewire 197. This embodiment allows for relatively independent movement of guidewire 197 after filter 190 has been deployed. Spring 195 also serves to provide the physician with a sense of increasing wire resistance if the guidewire is withdrawn too far proximally. Further, because of the flexibility of the tether, wire bias is decoupled from the filter, leading to excellent radial independence of filter position relative to wire motion.

Figure 20:
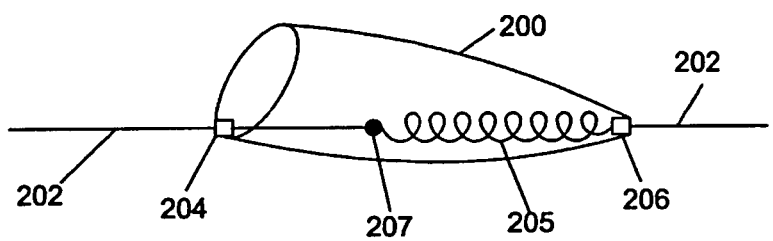

FIG. 20 is a schematic illustration of a filtration device of this invention comprising filter 200, proximal slider element 204 (disposed at the proximal end of the filter) and distal fixed element 206 (disposed at the distal end of the filter) disposed about guidewire 202. The slider element is configured to move freely over the guidewire. A shock absorber comprising a spring element 205 has a first end connected to distal fixed element 206 and a second end connected to guidewire 202 at point 207. Spring element 205 may be integrally formed from the guidewire or may be a separate element affixed to the guidewire. Some motion of the proximal end of wire 202 in either a proximal or distal direction will be accommodated without moving filter 200 by increasing or decreasing compression of spring element 205. Filter 200 will exhibit some resistance against the vessel wall in order to resist axial motion of guidewire 202 as transmitted through spring element 205. Thus, movement of the filter will not be caused unless guidewire movement is excessive.

Figure 21:
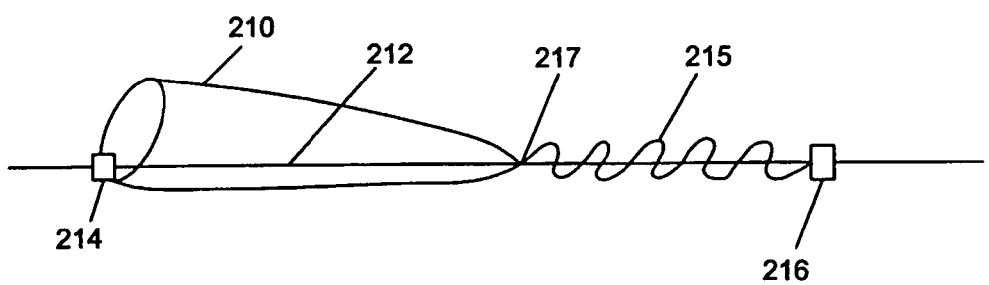

FIG. 21 is a schematic illustration of filter 210, proximal slider element 214 and distal fixed element 216 disposed about guidewire 212. Affixed to the filter's distal end 217 is spring element 215, which is attached to distal fixed element 216. Spring element 215 may be formed integrally with filter 210 or may be a separate component attached to distal end 217 and distal fixed element 216. Optionally, a distal slider can be incorporated at distal end 217 of the filter. Motion of the proximal end of wire 212 will be accommodated without moving filter 210 by increasing or decreasing compression of spring element 215. Filter 210 will exhibit some resistance against the vessel wall in order to resist axial motion of guidewire 212 as transmitted through spring element.

Figure 22:
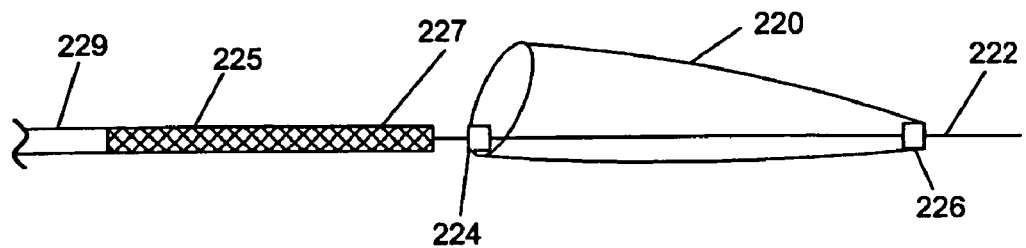

FIG. 22 is a schematic illustration of filter 220, proximal fixed element 224, and distal slider element 226 disposed about guidewire 222. Near the proximal end of filter 220, a shock absorber comprising braid 225 is attached to guidewire 222 at connection point 227 or alternatively to proximal fixed element 224. This connection point can be relatively close to proximal fixed element 224 (i.e., millimeters) or could be farther away (i.e., centimeters). Braid 225 is itself attached proximally to second guidewire 229. Braid 225 may be any desired length, preferably between about 10 to about 40 cm. Alternatively, shock absorber 225 could be a coil wound with spaces between adjacent coil windings. The braid in this embodiment is configured to lengthen or shorten to accommodate motion of second guidewire 229 without disturbing the filter placement. Further, because of the radial flexibility of the braid, wire bias is decoupled from the filter, leading to excellent radial independence of filter position relative to wire motion.

Figure 23:
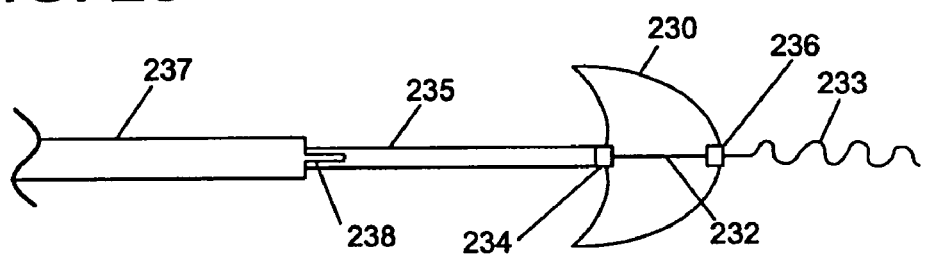

FIG. 23 is a schematic illustration of filter 230, proximal fixed element 234 and distal slider element 236 disposed about a first guidewire 232. The guidewire 232 ends distally at floppy tip 233 which provides an atraumatic and radiopaque terminus for the filter. Proximally, guidewire 232 is attached to elastomeric sleeve 235 which is attached proximally to a second guidewire 237, the distal end 238 of which is shown inside of elastomeric sleeve 235. Elastomeric sleeve 235 may be attached directly to guidewire 232 proximal to or at proximal fixed element 234. The elastomeric tube 235 can lengthen or shorten to accommodate wire 237 motion without disturbing the filter placement. The radial flexibility of the elastomeric sleeve decouples wire bias from the filter, leading to excellent radial independence of filter position relative to wire motion. Elastomeric tube 235 can be any desired length, preferably between about 10 to about 40 cm.

Figure 24:
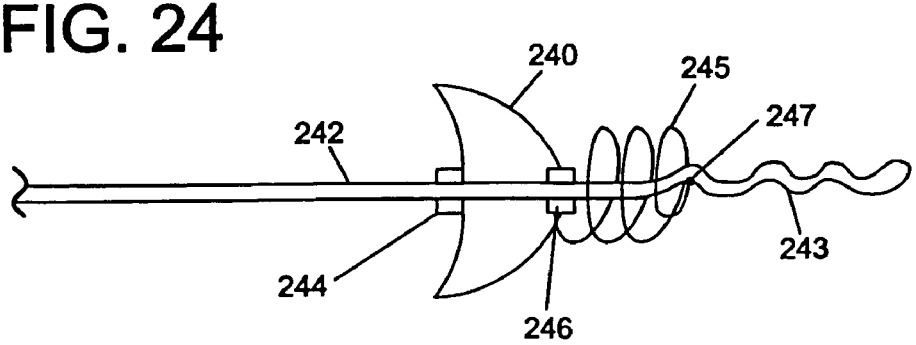

FIG. 24 is a schematic illustration of filter 240, proximal slider element 244, and distal slider element 246 disposed about guidewire 242. The guidewire ends distally at "floppy tip" 243. At the distal end of the filter, coil shock absorber 245 is attached to the distal element 246 proximally and to guidewire 242 distally at attachment point 247. Shock absorber 245 can be attached by any suitable means including welding or adhesives and serves to dampen the motion of the filter relative to the motion of the guidewire.

Figure 25:
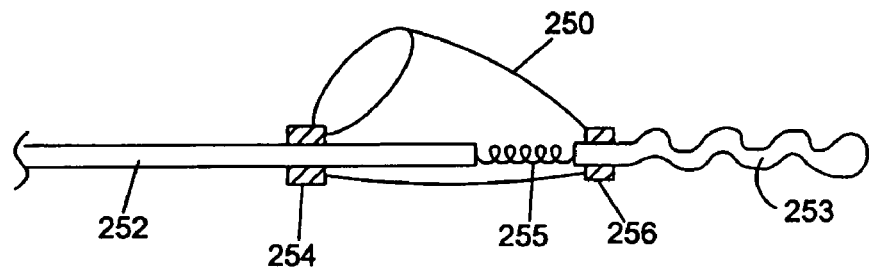

FIG. 25 is a schematic illustration of an embodiment with similarities to the embodiment of FIG. 24. Filter 250, and proximal slider element 254 are disposed about guidewire 252. Distal fixed element 256 is disposed about wire tip 253. The guidewire 252 ends distally at coil shock absorber 255.

The distal end of the filter 250 is attached to fixed element 256, to which is attached floppy tip 253 and also within filter 250 is attached shock absorber 255. Shock absorber 255 may be metallic or polymeric braid or coil, or an elastomeric material. It serves to damp the motion of the filter 250 relative to wire 252 in the proximal and distal directions.

Figure 26A:
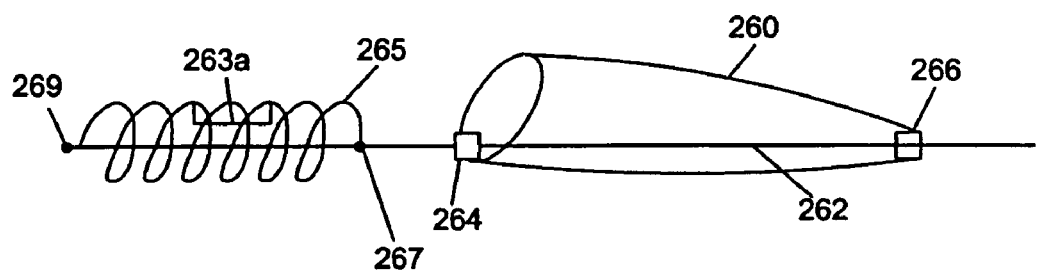
FIG. 26B is a detailed lengthwise cross-sectional view showing an alternative embodiment to that of FIG. 26A.

FIG. 26A is a schematic illustration of filter 260, proximal fixed element 264, and distal slider element 266 disposed about guidewire 262. Flexible coil 265 is attached to guidewire 262 proximal to fixed element 264 or can be attached directly to fixed element 264 by welding, adhesives, or with assistance of a crimped band. In the embodiment shown, coil 265 is attached to guidewire 262 at attachment point 267. Flexible coil 265 is also attached (at attachment point 269) near to proximal end of guidewire 262 by welding, adhesives, with assistance of a crimped band, or the like. Flexible coil 265 is a spring element. This includes conventional spring coils as well as serpentine, substantially planar coils, and flexible coil can be constructed of wire having round, flat, square, or other cross sectional shapes. Alternatively flexible coil 265 can be of braided construction or can be a tube from which material has been removed by way of etching, laser machining, grinding, electric discharge machining (EDM), and the like. Optional safety tether 263a is shown attached at proximal and distal locations of coil 265. More than one coil could be used in order to limit the axial extensibility of the flexible coil. Tether 263a desirably runs axially within the flexible coil 265.

Figure 26B:
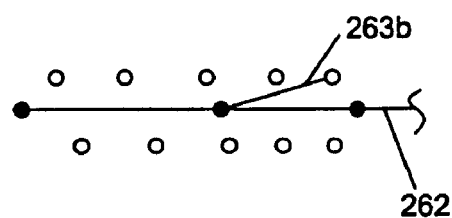

FIG. 26B shows a lengthwise cross sectional view of the coil, wherein tether 263b is attached to the coil and to guidewire 262. In either arrangement, the tether is used to limit the coil's extension.

Spring coil 265 is positioned on the guidewire so that once the filter of the embodiment of FIG. 26A or 26B is positioned in the vasculature, spring coil 265 will be at least partially outside of the body. The physician will handle the spring coil during catheter exchanges over the guidewire 262/spring coil 265 assembly. Motion of the spring coil will be absorbed by axial motion of adjacent coils so as to alter their spacing without causing motion of the filter relative to the vessel. Filter 260 will exhibit some resistance against the vessel wall in order to resist axial motion of guidewire 262 as transmitted through spring coil.

Figure 27:
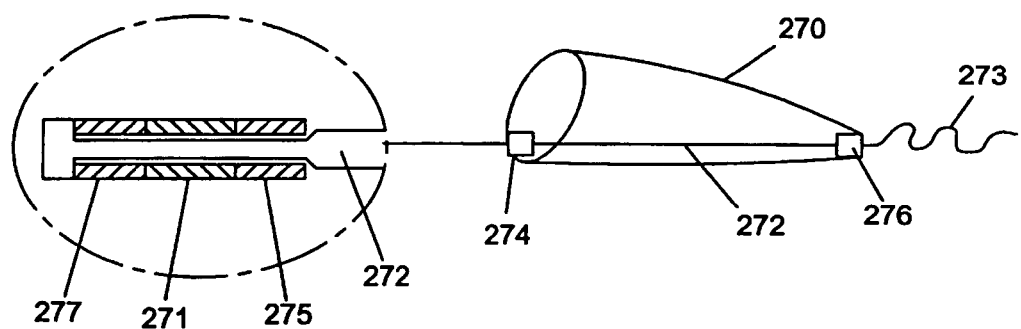

FIG. 27 is a schematic illustration of filter 270, proximal fixed element 274, and distal slider element 276 disposed about guidewire 272. The guidewire ends distally at floppy tip 273. Proximally, the guidewire extends through elastomeric tubes 275 and 277 and hypotube 271, shown in partial enlarged cross-sectional views. Elastomeric tubes are fused at one end to the end of hypotube 271 and at the other end to guidewire 272. The elastomeric tubes allow hypotube 271 to move without transmitting excessive motion to wire 272, effectively minimizing motion of filter 270 during movement of hypotube 271.

Locks

FIGS. 28 to 36 illustrate various embodiments of distal protection systems that incorporate a locking means having a locked configuration and an unlocked configuration. In the locked configuration the position of the functional element is fixed with respect to the guidewire being manipulated by the physician. This allows the physician to precisely manipulate and control the position of the functional device during delivery and retrieval of the functional device. In the unlocked configuration the guidewire is moveable within a desired range with respect to the functional element. This allows catheter exchanges and other treatment techniques performed during the intravascular procedure which can cause guidewire movement to be performed without dislodging or disrupting the functional device.

Figure 28A:
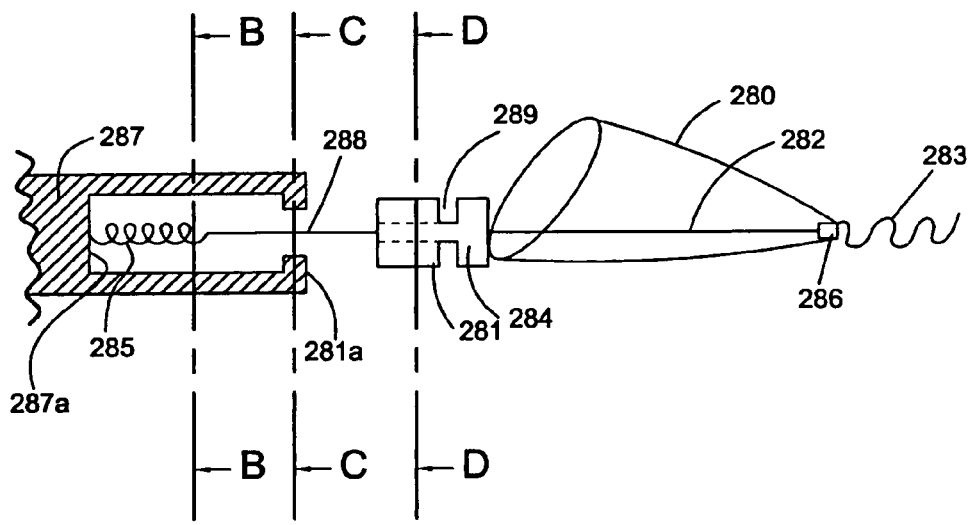
FIG. 28A is a schematic view and partial cross-sectional views of an alternate embodiment of the device of this invention having a guidewire locking feature.

FIG. 28A is a schematic illustration of a functional device which includes a filter 280, proximal fixed element 284, and distal slider element 286 disposed about guidewire 282. Proximal fixed element 284 is attached to tether 288 which is attached to a spring element 285 which itself is attached within a hollow core 287a of a second (host) guidewire 287. Floppy tip 283 extends distally from filter 280. In use, spring element 285 manages tether 288 so that excess tether is withdrawn into hollow core 287a of second guidewire 287. In the aforementioned respects the device of FIG. 28 is similar to the device of FIG. 19. Second guidewire 287 contains tabs 281a that are slideably received into longitudinal grooves 281 of proximal element 284. The grooves oppose each other, as shown in FIG. 28D. Proximal element 284 also contains circular groove 289 that can also slideably receive tabs 281a.

Figure 28B:
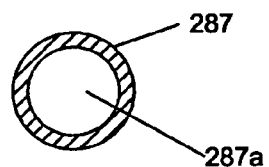
FIGS. 28B, 28C and 28D are cross-sectional views taken along lines B-B, C-C, and D-D, respectively of the device of FIG. 28A.
Figure 28C:
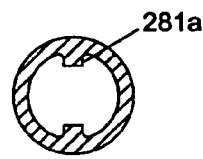
Figure 28D:
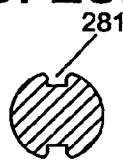

FIGS. 28B, 28C, and 28D are cross-sectional views taken along lines B-B, C-C, and D-D in FIG. 28. Tether 288 and spring element 285 are not shown. FIG. 28B shows hollow core 287a of guidewire 287. FIG. 28C illustrates tabs 281a that can be accepted in longitudinal grooves 281 of proximal element 284. FIG. 28C illustrates opposing longitudinal grooves 281 on proximal element 284. In this embodiment, two tabs are shown. In other embodiments, one or more tabs can be used. Alternatively, tabs can be located on fixed element 284 and cooperating grooves located on wire 287.

To deliver the filter, proximal element 284 is inserted into hollow core 287a, and tabs 281a are slideably engaged into grooves 281. The tabs are advanced distally relative to proximal element 284 until the tabs reach circular groove 289, at which point guidewire 287 is rotated relative to proximal element 284 to cause the tabs to enter circular groove 289. In this configuration wire 287 is locked to proximal element 284 and filter 280. The filter can be precisely placed at a desired location in the vasculature when the guidewire is locked in this configuration.

Once the filter is placed, wire 287 is rotated relative to proximal element 284 until the tabs align with longitudinal grooves 281. The wire is then withdrawn to disengage the tabs from the proximal element. The wire may be further withdrawn to take full advantage of the tether and its ability to decouple wire motion from filter position. Because of the flexibility of the tether, wire bias is decoupled from the filter, leading to excellent radial independence of filter position relative to wire motion. To recover the filter the reverse of the above steps is performed in order to once again lock the wire into the proximal element. Alternatively a catheter sheath can simply be advanced over the wire, tether, and filter, or the same can be withdrawn into a catheter sheath.

Figure 29A:
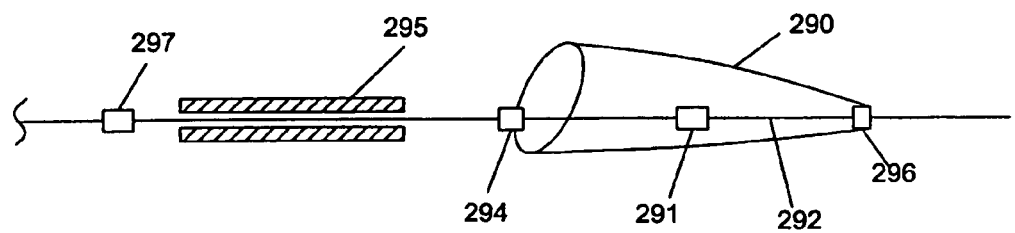
FIG. 29A is a schematic view of a further alternate embodiment of the device of this invention having a guidewire locking feature.

FIG. 29A is a schematic illustration of filter 290, distal slider element 296, and proximal slider element 294, and stop 291 disposed about the wire 292. Proximally, wire 292 extends through hollow tube or sleeve 295 (shown in cross section as indicated by cross hatching) to a locking stop 297 which is moveable over wire 292 and is configured so it can be locked in place on the guidewire at a desired location. Locking stop 297 can be constructed of an elastomeric cylinder axially slit partway through the cylinder diameter or in any of a number of ways as is apparent to those skilled in the art. To control the placement of the filter in the vasculature, filter 290 is held against sleeve 295 by pulling wire 292 proximally relative to tube 295, until proximal element abuts the distal end of tube 295, and then locking the tube in this relative position by sliding locking stop 297 distally relative to the guidewire until the stop abuts the proximal end of the tube. After the filter is in place, locking stop 297, which is located outside of the patient, is loosened by sliding proximally, allowing the filter to "float" while still tethered to the wire. Tube 295 may be withdrawn slightly to take full advantage of the range of motion allowed by this design in its ability to decouple the tube motion from the filter position. The length of tube 295 is sufficient such that during use the proximal end of tube 295 extends outside the patient and the distal end of tube 295 within the body, preferably extends to the treatment site. Thus, catheter exchanges can be made over tube 295 without disrupting or moving filter 290.

Figure 29B:
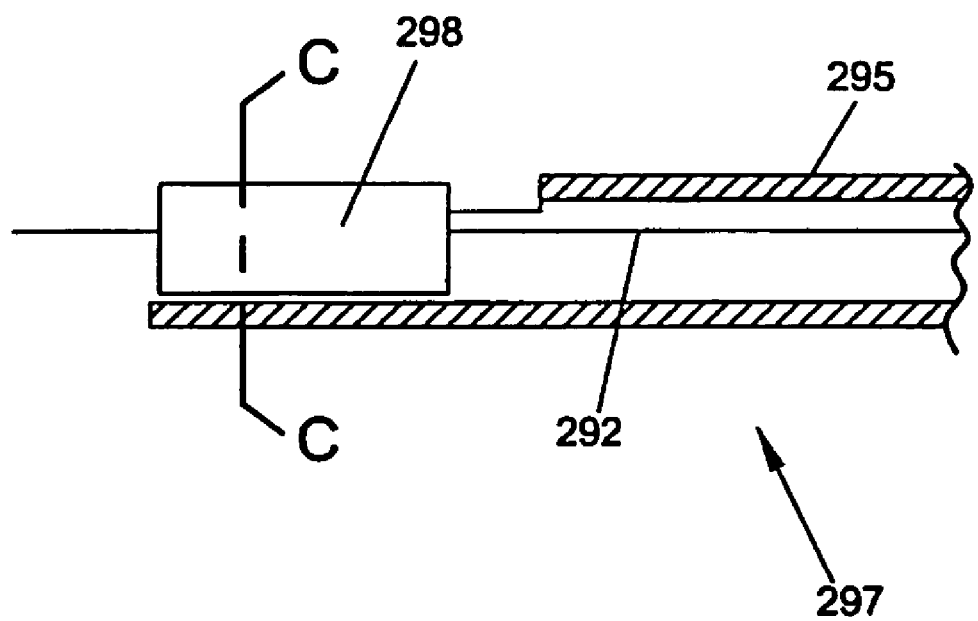
FIG. 29B is a partial view showing detail of the device of FIG. 29A.
Figure 29C:
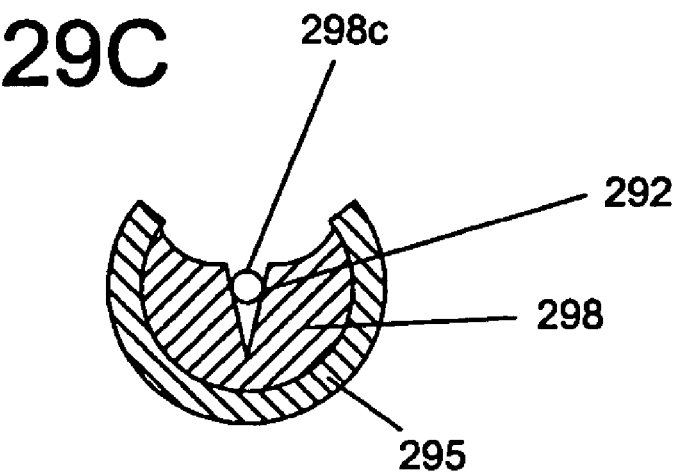
FIG. 29C is a cross-sectional view along line C-C in FIG. 29B.

An alternate embodiment of locking stop 297 is shown in FIGS. 29B and 29C. FIG. 29B is a detail cross-sectional view of locking stop 297 which comprises friction stop 298 attached to sleeve 295. FIG. 29C is a cross-sectional view along line C-C of FIG. 29B. Friction lock 298 contains slit 298c which is adapted to compressively (and reversibly) receive wire 292. Space is provided distal to friction lock 298 to allow wire 292 to emerge from sleeve 295. A friction lock can be made of any elastomeric material such as polyamide block copolymers (commercially available under the trade designation "PEBAX"), polyurethane, silicone, rubbers, and the like. Slit 298c is preferably smaller in width than the diameter of wire 292.

In use, wire 292 is pulled proximally until the proximal element 294 abuts against the distal end of sheath 295. Wire 292 is then pressed into slit 298c of lock 298. In this embodiment, coincidentally, stop 291 will be in contact with and immediately distal to proximal element 294, although this is not necessary in other designs with fixed proximal elements. With the wire locked into slit 298c the device can be advanced into the body and the filter placed with precision at a predetermined location. To release the filter, the wire is lifted out of the slit in the friction lock and preferably sleeve 295 is withdrawn a short distance proximally to establish distance between the distal end of the sleeve and the proximal element.

Figure 30A:
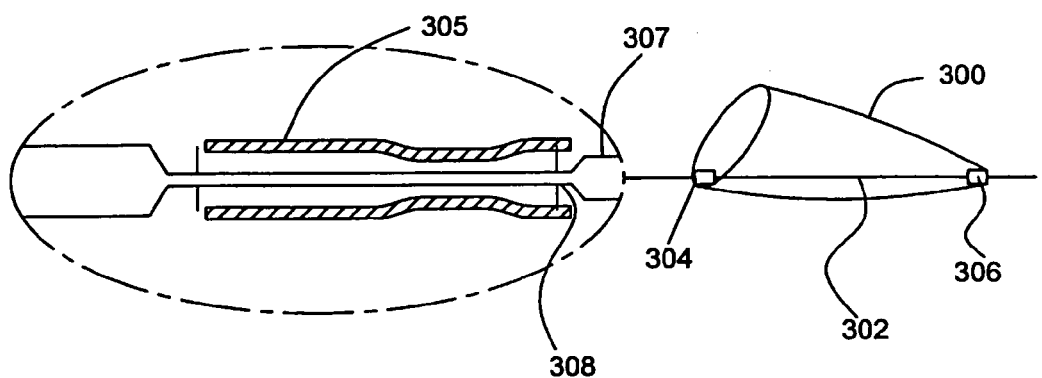
FIG. 30A is a schematic view and a partial cross-sectional view of another alternate embodiment of the device of this invention having a guidewire locking feature.
Figure 30B:
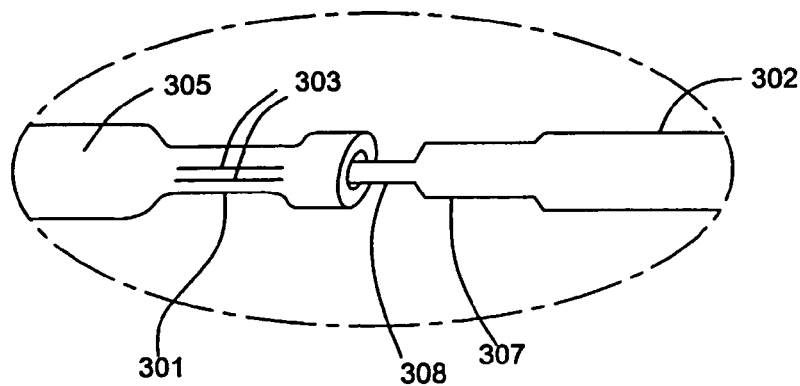
FIG. 30B is a partial schematic view of a portion of the device of FIG. 30A.

FIGS. 30A and 30B illustrate a lock that can be fitted to devices similar to the device described in FIG. 11. Filter 300, proximal fixed element 304, and distal slider element 306 are disposed about guidewire 302, which extends proximally through hypotube 305. Hypotube 305 is shown in cross-section (as indicated by cross hatching), disposed about guidewire 302. FIG. 30B is a perspective view that shows in detail that hypotube 305 has two slits 303 disposed distally and are located in a reduced diameter portion 301 of the hypotube. The reduced diameter portion of the hypotube is preferably formed by deforming the slit region radially inwardly. The hypotube is biased radially inwardly about the slits. It should be noted that more than one slit could be used, and that the position of these slits may be varied. Wire 302 has a reduced diameter portion 308 which is slideably received within the hypotube including within the reduced diameter slit portion of the hypotube, and an intermediate diameter portion 307 which is slideably received within the hypotube but is frictionally engaged within region 301 of the hypotube. It is understood that the wire regions and tube slits can be arranged in other orders by one skilled in the art so as to achieve the objects of this invention. It is further understood that the slits can be axial, helical, or circumferential and may be of full or partial thickness. It is further understood that slits may not be necessary, simply rendering the tube non-circular in cross section may also achieve the desired goal. The frictional engagement of intermediate diameter portion within region 301 of the hypotube acts as a lock to the motion of the wire.

In use, the hypotube and wire are frictionally engaged by moving the hypotube distally until portion 307 is engaged in region 301 of the hypotube so as to lock the filter relative to the tube. The filter can then be positioned within the body in a reliable and accurate manner. The tube and wire are then released from their frictional engagement by holding the proximal end of guidewire 302 while moving the hypotube proximally to disengage portion 307 from region 301. Once released, the hypotube may be moved independently of guidewire 302 and filter 300 over portion 308 of the guidewire.

Figure 31A:
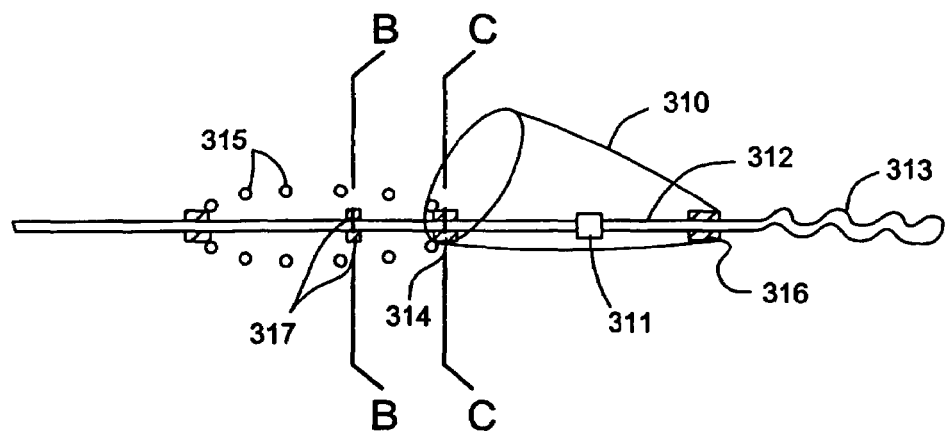
FIG. 31A is a schematic view of a further alternate embodiment of the device of this invention having a guidewire locking feature.
Figure 31B:
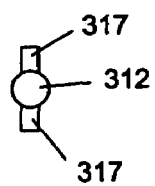
FIGS. 31B and 31C are cross-sectional views of the device of FIG. 31A along lines B-B and C-C, respectively.
Figure 31C:
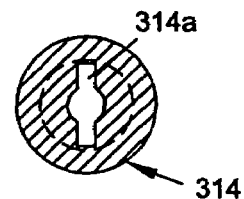
Figure 31D:
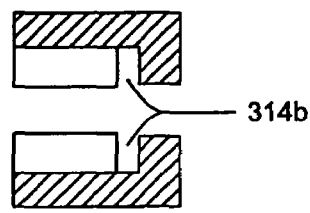
FIG. 31D is a planar cross-sectional view.

FIGS. 31A-31D are schematic illustrations of a distal protection device including a filter 310, proximal slider element 314, and distal slider element 316 disposed about guidewire 312. Distally, guidewire 312 ends at floppy tip 313. Optional stop 311 is affixed to guidewire 312 within the filter region, illustrated in the drawing at a midpoint of this region. Wire 312 and proximal slider element 314 are configured so that guidewire 312 can be engaged with proximal slider 314 during delivery and deployment of filter 310 and disengaged during performance of the procedure to allow the guidewire 312 to move independently of the filter. Shock absorber 315 comprises a sleeve of elastomer, braid, spring coil, or the like. Tabs 317 are attached to wire 312 within shock absorber 315. Proximal slider element 314 is provided with linear grooves 314a as best seen in FIG. 31C, which is a cross-sectional view of the proximal slider taken along line C-C in FIG. 31A. FIG. 31D is an enlarged (side) cross-sectional view of slider element 314 shown in FIG. 31A which shows annular internal recess 314b, which slideably receives tabs 317. To controllably position the filter, tabs 317 are advanced through the linear grooves until they are within the annular internal recess. Guidewire 312 is then rotated such that tabs 317 engage the annular internal recess. In this configuration there is positive engagement between the proximal slider element 314 and the wire 312, and the filter can be precisely placed in any desired anatomical location. After placement the guidewire 312 is rotated such that tabs 317 align with and engage the linear grooves and the guidewire 312 is retracted until the tabs 317 are free of the proximal slider element 314. In this configuration the wire 312 is able to move without disturbing the position of filter 310 and the shock absorber is positioned to provide the physician with a feeling of increased resistance if the guidewire is moved distally to a position where the shock absorber approaches the filter.

Figure 32:
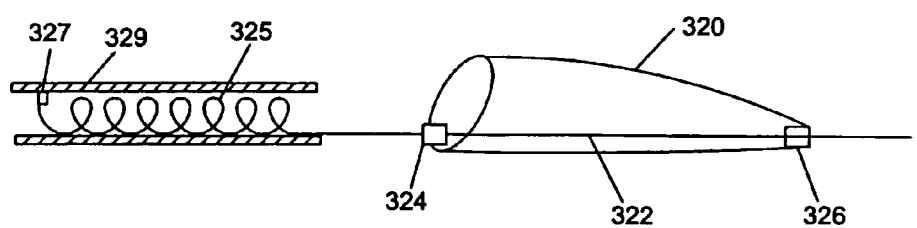
FIGS. 32 to 35 are schematic and partial cross-sectional views of still further alternate embodiments of the device of this invention equipped with a guidewire locking feature.
Figure 33:
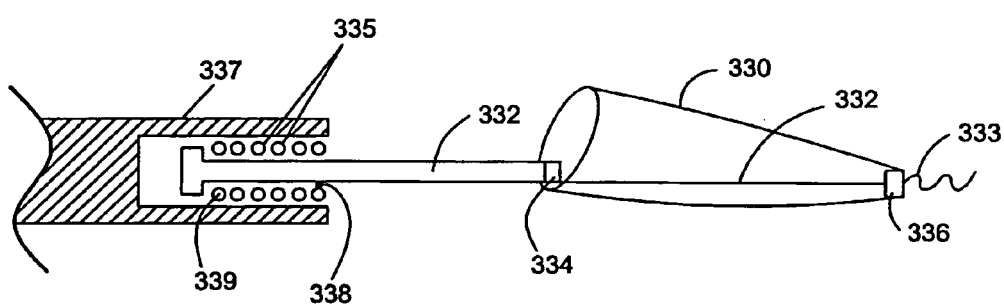

FIGS. 32 and 33 illustrate two embodiments of a coil wire clutch locking mechanism.

FIG. 32 illustrates filter 320, proximal fixed element 324, and distal slider element 326 disposed about guidewire 322. The guidewire extends proximally to coiled wire or spring 325 attached (at point 327) to and disposed within hollow guidewire 329. Hollow guidewire may be hollow throughout its length or may be hollow over only a portion of its length. The hollow guidewire can be twisted during movement and deployment of the filter to control the movement of the filter.

Specifically, the filter is locked into position by twisting the hollow wire in a direction that tends to enlarge the diameter of the coil. Friction of the filter against the vessel wall will tend to resist this rotation, allowing the coil to lock within the hollow wire. Once locked the hollow wire and filter can be moved as a unit and the filter placed at an exact location within the body. To release the filter from the wire the wire is counter-rotated so as to decrease the coil diameter and thereby allow axial motion of the coil within the hollow wire.

FIG. 33 is a schematic illustration of filter 330, proximal fixed element 334, and distal slider element 336 disposed about guidewire 332, which ends distally at floppy tip 333. The left side of the drawing is shown in a cross-sectional view, and the scale is exaggerated to show detail. Proximally, guidewire 332 extends to and is attached within hollow host guidewire 337, which is fitted with spring coil 335. One end of spring coil 335 attaches at attachment point 339 to interior of hollow guidewire 337 and the opposite end of spring coil 335 attaches at attachment point 338 on the exterior of guidewire 332. Coil 338 is biased to allow free axial translation of wire 332. In operation, wire 332 can translate axially relative to hollow wire 337. To fix wire 332 relative to hollow wire 337, hollow wire 337 is twisted in either direction relative to wire 332 such that coil 335 tends to diametrically compress, locking onto wire 332, or to diametrically expand, locking within hollow wire 337. Frictional engagement of filter 330 relative to the vessel will provide the needed counter rotational force for coil clutch actuation.

It is understood that it may be advantageous to make hollow wire 337 hollow over its entire length and to extend wire 332 proximally such that it extends from proximal end of hollow wire. This configuration will allow wire 332 to be held stationary while hollow wire 337 is rotated to engage the coil clutch. This embodiment eliminates the need for filter 330 to resist rotational motion relative to the vessel. Advantageously rotational friction between wire 332 and hollow wire 337 will hold the relative rotation between the two wires such that the assembly can be left in either a locked or an unlocked position. Friction between the wires can be augmented by any of a number of seals as would be obvious to those skilled in the art. An advantage of this design as compared to other lock designs is that the hollow wire need not be advanced relative to the filter in order to lock the wire relative to the filter, rather, a simple rotation of the pertinent elements will suffice.

Figure 34:
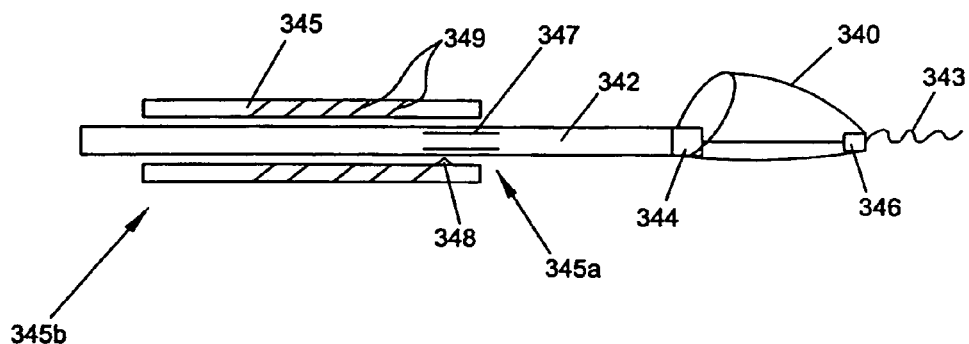

FIG. 34 has elements similar to that of the embodiment of FIG. 33. In this embodiment, a spiral cut tube 345 shown in cross-section is used to control wire motion. Similarly to FIG. 33, the left portion of this drawing is shown in a cross-sectional view, and the scale is exaggerated to show detail. Filter 340, proximal fixed element 344, and distal slider element 346 are disposed about guidewire 342, which ends distally at floppy tip 343. Proximally, the guidewire extends through spiral cut tube 345. Guidewire 342 has splines 347 and tube 345 has one or more teeth 348 which are configured to slideably engage the splines. Spiral cuts 349 preferably extend through the full thickness of tube 345 except at proximal end 345a where the uncut tube serves as a handle and at distal end 345b where the uncut tube serves to prevent diametrical enlargement of tube and thereby preserving slideable engagement of the teeth in the splines.

To fix the wire relative to the tube, the proximal end of the wire and the tube are twisted relative to one another so as to cause the diameter of the spiral cut tube to shrink tightly about the wire. For example, the proximal end of the tube is twisted clockwise. The clockwise rotation of the tube's distal end is resisted since the teeth are engaged in the splines of the guidewire to prevent the distal end of the tube from rotating. To release the wire relative to the tube these elements are counter-rotated so as to restore or increase the diameter of the spiral cut tube so that the wire is once again slideably received within the tube.

It will be understood by those skilled in the art that it is advantageous to employ frictional locks similar to those discussed in connection with FIG. 33 so as to maintain either the locked or unlocked position, or both, of tube relative to wire.

Figure 35:
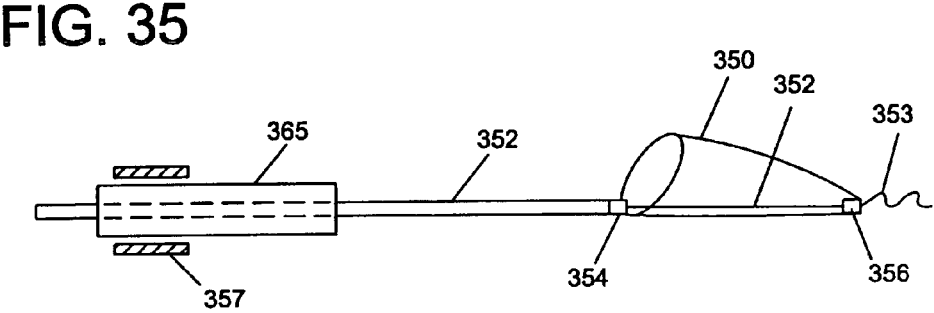

FIG. 35 is a schematic illustration of filter 350, proximal fixed element 354, and distal slider element 356 disposed about guidewire 352, which ends distally at floppy tip 353. Guidewire 352 is shown (dotted line) extending proximally through tube 355, which is shown in an exaggerated scale. Guidewire 352 is provided with a curvature or bend by, for example, heat setting, or simply by plastically deforming the wire. Once inserted in tube 355, guidewire 352 can be used in cooperation with tube 355 to alternately lock the position of filter 350 relative to tube 355 or to allow slideable decoupling of tube 355 position relative to filter 350. In use, tube 355 can be slid over the bent wire to axially lock the two, and tube 355 can be oppositely slid relative to wire 352 to unlock the two.

Alternatively the bend can be set or heat set into tube 355. In this embodiment, collar 357 surrounds tube 355 and serves to straighten the tube so as to allow slideable motion between wire 352 and tube 355. When collar 357 is positioned away from the bent portion of tube 355 there is frictional engagement of tube 355 relative to wire 352 and axial motion between the two is eliminated.

Figure 36A:
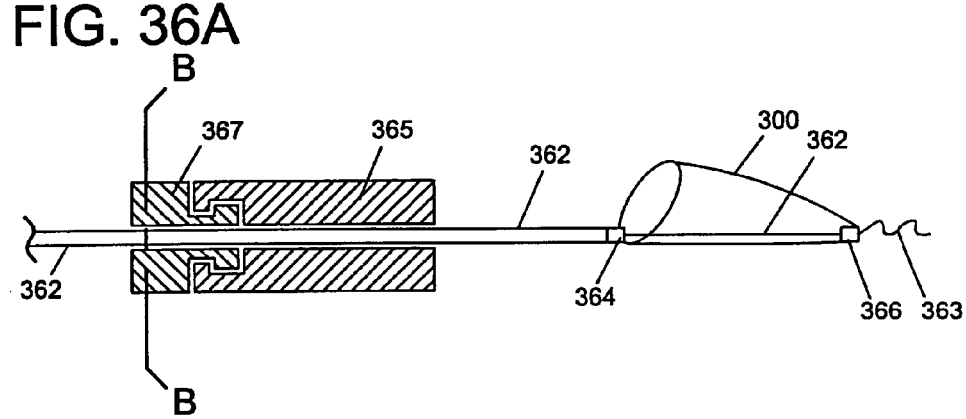
FIG. 36A is a schematic view of a further alternate embodiment of the device of this invention having a guidewire locking feature and FIGS. 36B and 36C are cross-sectional views of the device of FIG. 36A along line B-B.
Figure 36B:
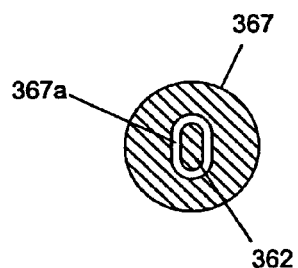
Figure 36C:
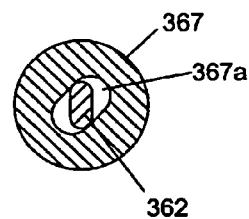
Figure 37:
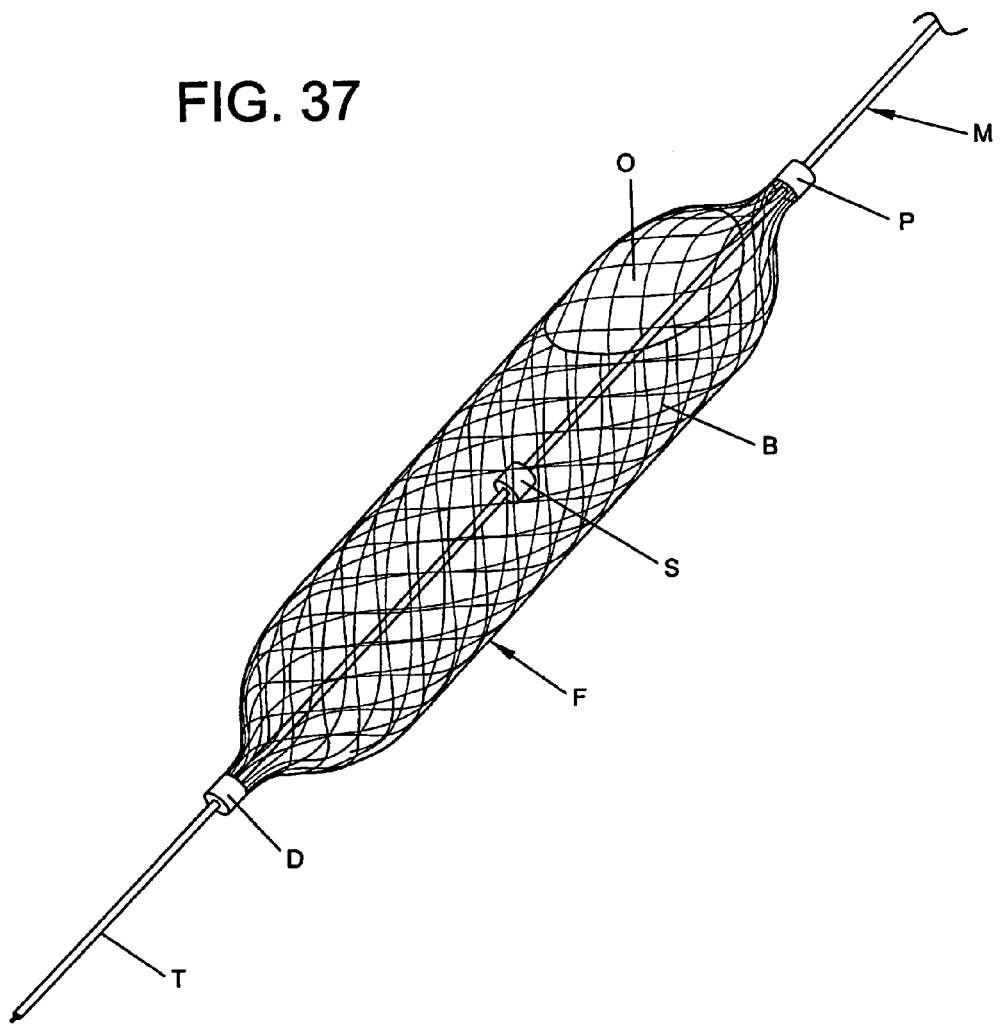
FIG. 37 is a perspective view of a Prior Art distal protection filtration device.

FIG. 36A is a schematic illustration of an embodiment with elements similar to that of FIG. 35, and again the left portion of the drawing is shown in exaggerated scale to illustrate detail. Filter 360, proximal fixed element 364, and distal slider element 366 are disposed about guidewire 362, which ends distally at floppy tip 363. In this case guidewire 362 has an oval cross-section over at least a portion of its proximal length and extends though tube 365. This is shown in cross-sectional view in FIG. 36B taken along line B-B in FIG. 36A. Tube 365 is rotationally affixed proximally to tubular lock 367. Tubular lock 367 also has an interior lumen 367a with an oval cross section that slideably engages the oval portion of wire 362. Lock 367 is engaged by rotating lock 367 relative to wire 362 (as shown in FIG. 36C) such that a frictional engagement both prevents axial motion of the wire relative to tube and rotational motion of lock relative to wire. The lock is disengaged by counter-rotation of lock relative to wire.

A non-filtering occlusive embolic protection device can be built with lockable wire motion by simply incorporating a balloon instead of the filter element and a hollow wire with valve instead of a solid wire in designs similar to those described in connection with FIGS. 30, 33, 34, 35, and 36.

OTHER EMBODIMENTS

One embodiment of this invention illustrated in FIG. 14A is an occlusive device comprising a balloon catheter. Other elements, as taught above, can be incorporated into this device, depending upon the desired characteristics. A shock absorber on a balloon catheter can easily be constructed by combining the shock absorber illustrated in FIG. 27 with the balloon and valve teachings of FIG. 14. Similarly a balloon protection device can be readily made based on the description in FIG. 26 by substituting a balloon for the filter 260 and using a hollow guidewire 262 for inflation of the balloon. Similarly the device of FIG. 19 can be adapted to balloon construction by using hollow versions of the wire 197, spring 195, and tether 198. The device of FIG. 22 can be adapted to a balloon device by adding a hollow coiled tube within the braid 225 and by connecting the interior path of said coiled tube with the interior of the balloon and the channel within a hollow wire 229. FIGS. 24 and 25 can also be adapted to balloon protection devices by using a hollow wire, adding a slideable seal to proximal sliding element, and adding a communicating pathway between interior of hollow wire and interior of balloon. This pathway might include the interstices of the braid, coil, or other shock absorber.

The protection device of this invention is particularly useful in the prevention of distal embolization of debris liberated during interventional procedures such as in cardiology, radiology, and neuroradiology procedures.

Although particular embodiments of the invention have been disclosed herein in detail, this has been done for the purposes of illustration only, and is not intended to be limiting with respect to the scope of the appended claims. It is contemplated that various substitutions, alterations, and modifications may be made to the embodiments of the invention described herein without departing from the spirit and scope of the invention as defined by the claims.

What is claimed is:

1. A distal protection device for use in a body lumen comprising:
    a first elongate member having distal and proximal ends;
    a second elongate member having distal and proximal ends; and
    a functional element carried by the second elongate member, the functional element being expandable from a delivery configuration to an expanded deployed configuration when the functional element is deployed in the body lumen,
    the first elongate member having a tubular body having a lumen with an interior diameter and the second elongate member having a first region with an exterior diameter less than the interior diameter of the lumen of the tubular body, the first region being slideably received in the lumen of the tubular body,
    the first and second elongate members being moveable over a range of motion from a first relative position to a second relative position such that when the functional element is deployed in the body lumen the first elongate member may be moved without resulting in corresponding movement of the functional element, the distal end of the second elongate member being distal to the distal end of the first elongate member over the entire range of motion,
    the second elongate member having enlarged portions adjacent proximal and distal ends of the first region, the enlarged portions having exterior diameters larger than the interior diameter of the lumen of the tubular body,
    wherein the first elongate member has an exterior diameter, and the exterior diameter of the first elongate member and the exterior diameters of the enlarged portions of the second elongate member are approximately equal.

2. The distal protection device of claim 1 wherein the functional element comprises a filter having a body defining a proximally facing opening when in the expanded deployed configuration.

3. The distal protection device of claim 1 wherein the functional element comprises a filter.

4. The distal protection device of claim 1 wherein the functional element comprises an occlusive element.

5. The distal protection device of claim 1 wherein the functional element comprises an inflatable balloon.

6. The distal protection device of claim 1 wherein at the first relative position a first surface of the first elongate member abuts against a first surface of the second elongate member.

7. The distal protection device of claim 1 further comprising brake elements at the distal and proximal ends of the first elongate member.

8. The distal protection device of claim 7 wherein the brake elements comprise a spring.

9. The distal protection device of claim 7 wherein the brake elements comprise an elastomer.

10. The distal protection device of claim 7 wherein the brake elements comprise a magnet.

11. The distal protection device of claim 1 further comprising a locking element for locking the first elongate member to the second elongate member, the locking element having a locked position where the relative positions of the first and second elongate members are locked and an unlocked position where the first elongate member can be moved over the range of motion from the first relative position to the second relative position without resulting in movement of the second elongate member.

12. The distal protection device of claim 1 further comprising a locking element for locking the first elongate member to the second elongate member, the locking element having a locked position where the relative positions of the first and second elongate members are locked and an unlocked position where the first elongate member can be moved over the range of motion from the first relative position to the second relative position without resulting in movement of the second elongate member when the functional element is deployed.

13. The distal protection device of claim 1 further comprising a locking element for locking the first elongate member to the second elongate member, the locking element having a locked position where the relative positions of the first and second elongate members are locked and an unlocked position where the first elongate member can be moved over the range of motion from the first relative position to the second relative position without resulting in movement of the functional element when the functional element is deployed.

14. The distal protection device of claim 1 wherein the tubular body of the first elongate member has a constant diameter.

15. The distal protection device of claim 1 wherein the tubular body of the first elongate member comprises a reduced diameter portion.

16. The distal protection device of claim 11 wherein the locking element comprises a reduced diameter portion of the first elongate member.

17. The distal protection device of claim 16 wherein the reduced diameter portion comprises one or more slits.

* * * * *